US011802149B2

(12) United States Patent
Liao et al.

(10) Patent No.: US 11,802,149 B2
(45) Date of Patent: Oct. 31, 2023

(54) ANTI-AMYLOID BETA ANTIBODIES AND METHODS OF USING THE SAME

(71) Applicant: AbbVie Inc., North Chicago, IL (US)

(72) Inventors: Fan Liao, Belmont, MA (US); Meha Chhaya, Shrewsbury, MA (US); Andrew J. McCluskey, Holden, MA (US); Nathan J. Brown, Wayland, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 18/050,553

(22) Filed: Oct. 28, 2022

(65) Prior Publication Data

US 2023/0203143 A1    Jun. 29, 2023

Related U.S. Application Data

(60) Provisional application No. 63/263,204, filed on Oct. 28, 2021.

(51) Int. Cl.
 *C07K 16/18* (2006.01)
 *A61P 25/28* (2006.01)
 *C12N 15/79* (2006.01)

(52) U.S. Cl.
 CPC .............. *C07K 16/18* (2013.01); *A61P 25/28* (2018.01); *C12N 15/79* (2013.01); *C07K 2317/52* (2013.01); *C07K 2317/565* (2013.01)

(58) Field of Classification Search
 None
 See application file for complete search history.

(56) References Cited

U.S. PATENT DOCUMENTS 8,715,657 B2    5/2014    Bardroff et al.
2013/0236471 A1    9/2013    Brown et al.

FOREIGN PATENT DOCUMENTS

WO    WO-2012136552 A1    10/2012

OTHER PUBLICATIONS

Aisen P.S., et al., "The Future of Anti-Amyloid Trials," The journal of Prevention of Alzheimer's Disease, 2020, vol. 7(3), pp. 146-151.
Greenberg S.M., et al., "Cerebral Amyloid Angiopathy and Alzheimer Disease—One Peptide, Two Pathways," Nature Reviews Neurology, 2020, vol. 16(1), pp. 30-42.
Haenseler W., et al., "A Highly Efficient Human Pluripotent Stem Cell Microglia Model Displays a Neuronal-Co-culture-Specific Expression Profile and Inflammatory Response," Stem Cell Reports, 2017, vol. 8(6), pp. 1727-1742.
Janssens J., et al., "Passive Immunotherapy with a Novel Antibody Against 3pE-Modified Aβ Demonstrates Potential for Enhanced Efficacy and Favorable Safety in Combination with BACE Inhibitor Treatment in Plaque-Depositing Mice," Neurobiology of Disease, 2021, vol. 154:105365, pp. 1-8.
Jawhar S., et al., "Pyroglutamate Amyloid-β (Aβ): A Hatchet Man in Alzheimer Disease," The Journal of Biological Chemistry, 2011, vol. 286(45), pp. 38825-38832.
Kabat E.A., et al., "Accession No. PS91-192898, Sequences of Proteins of Immunological Interest," National Institutes of Health Publication No. 91-3242, 5th Edition, 1991, pp. 647-669.
Kaufman R.J., et al., "Amplification and Expression of Sequences Cotransfected with a Modular Dihydrofolate Reductase Complementary DNA Gene," Journal of Molecular Biology, 1982, vol. 159(4), pp. 601-621.
Kuo Y.M., et al., "Isolation, Chemical Characterization, and Quantitation of Aβ 3-Pyroglutamyl Peptide from Neuritic Plaques and Vascular Amyloid Deposits," Biochemical and Biophysical Research Communications, 1997, vol. 237(1), pp. 188-191.
Penninkilampi R., et al., "Safety and Efficacy of Anti-Amyloid-β Immunotherapy in Alzheimer's Disease: A Systematic Review and Meta-Analysis," Journal of Neuroimmune Pharmacology, 2017, vol. 12(1), pp. 194-203.
Radde R., et al., "Aβ42-driven Cerebral Amyloidosis in Transgenic Mice Reveals Early and Robust Pathology," EMBO Rep., 2006, vol. 7(9), pp. 940-946.
Selkoe D.J., et al., "The Amyloid Hypothesis of Alzheimer's Disease at 25 Years," EMBO Molecular Medicine, 2016, vol. 8(6), pp. 595-608.
Silva J.P., et al., "The S228P Mutation Prevents in Vivo and in Vitro IgG4 Fab-arm Exchange as Demonstrated Using a Combination of Novel Quantitative Immunoassays and Physiological Matrix Preparation," Journal of Biological Chemistry, 2015, vol. 290(9), pp. 5462-5469.
Sperling R.A., et al., "Amyloid-Related Imaging Abnormalities in Amyloid-Modifying Therapeutic Trials: Recommendations from the Alzheimer's Association Research Roundtable Workgroup," Alzheimer's & Dementia, 2011, vol. 7(4), pp. 367-385.
Urlaub G., "Isolation of Chinese Hamster Cell Mutants Deficient in Dihydrofolate Reductase Activity," Proceedings of the National Academy of Sciences of the United States of America, 1980, vol. 77(7), pp. 4216-4220.
U.S. National Library of Medicine., "A Study of LY3002813 in Participants with Early Symptomatic Alzheimer's Disease (Trailblazer-Alz)," NCT03367403, 2017.
U.S. National Library of Medicine., "221AD302 Phase 3 Study of Aducanumab (BIIB037) in Early Alzheimer's Disease (Emerge)," NCT02484547, 2015.
Van Dyck C.H., "Anti-Amyloid-β Monoclonal Antibodies for Alzheimer's Disease: Pitfalls and Promise," Biological Psychiatry, 2018, vol. 83(4), pp. 311-319.
Wilgenburg B.V., "Efficient, Long Term Production of Monocyte-Derived Macrophages from Human Pluripotent Stem Cells Under Partly-Defined and Fully-Defined Conditions," PLOS one, Aug. 12, 2013, vol. 8(8): e71098.
International Search Report and Written Opinion for Application No. PCT/US2022/078913, dated Jan. 31, 2023, 8 pages.

*Primary Examiner* — Adam Weidner
(74) *Attorney, Agent, or Firm* — Elias C. Sayre

(57) ABSTRACT

The present inventive concept is related to antibodies, such as recombinant humanized and monoclonal antibodies, methods of making antibodies, and methods of using antibodies, such as antibodies directed toward and capable of specifically binding to and clearing amyloid-beta (Aβ) plaques in the brain that are suitable for use in the treatment of disorders such as Alzheimer's Disease (AD).

6 Claims, 6 Drawing Sheets

Figure 1:
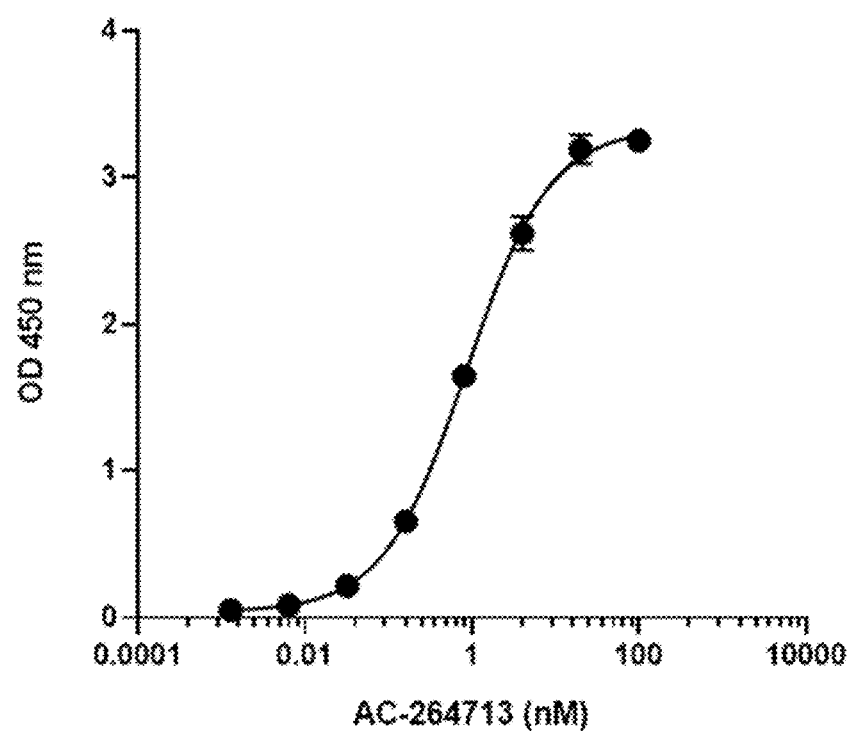

Specification includes a Sequence Listing.

**** P < 0.0001 for comparison of concentrations a, b or c µg/mL to 0 ug/mL (One-way ANOVA followed by Dunnett's multiple comparisons test).

ANTI-AMYLOID BETA ANTIBODIES AND METHODS OF USING THE SAME

1. CROSS REFERENCE TO RELATED APPLICATIONS

The instant application claims the benefit of U.S. Provisional Patent Application Ser. No. 63/263,204, filed Oct. 28, 2021, the content of which is incorporated by reference herein in its entirety.

2. REFERENCE TO AN ELECTRONIC SEQUENCE LISTING

Incorporated herein by reference in its entirety is a Sequence Listing entitled, "ABV21397USO1_ST26.xml", comprising SEQ ID NO: 1 through SEQ ID NO: 37, which includes the amino acid and DNA sequences disclosed herein. The Sequence Listing has been submitted electronically in XML format. The Sequence Listing was created on Oct. 27, 2022, and is 22,528 bytes in size.

3. TECHNICAL FIELD

The present application pertains to, among other things, anti-amyloid beta (AD) antibodies and methods of making and using the same.

4. BACKGROUND

The amyloid hypothesis of Alzheimer's disease (AD) suggests that an imbalance between clearance and production of Aβ results in the protein accumulating in the brain; this initiates several downstream events that ultimately lead to neuron and synapse loss, manifesting in the clinical symptoms of AD (Selkoe and Hardy 2016). Recent drug development for the treatment of AD has focused on compounds that reduce both soluble, monomeric, and insoluble, deposited forms of AD, with several mAbs that bind to different forms of Aβ having been tested in the past two decades (van Dyck 2018). Passive immunotherapy predominantly underlies the approach of administering anti-Aβ mAbs for the treatment of AD, as the mAbs bind to Aβ to stimulate an immune response that aids in clearing the protein.

Historically, mAbs targeting Aβ have failed to demonstrate efficacy in slowing cognitive and functional decline in AD. However, these trials have yielded important data related to safety. Moreover, these studies have provided insight into the specific forms of Aβ that may need to be targeted to slow AD progression, leading many to believe Aβ is still an appropriate target for developing AD therapies (van Dyck 2018); (Aisen, Cummings et al. 2020). Indeed, recent results from a Phase 3 trial of aducanumab (NCT02484547) and a Phase 2 trial of donanemab (NCT03367403), both mAbs targeting Aβ, suggest that this class of compounds may be efficacious in treating AD. Thus, given the scientific support for the amyloid hypothesis of AD and the positive signal seen in recent trials of anti-A mAbs, development of new anti-Aβ mAbs offer further promise in the search for effective AD treatments.

Anti-Aβ mAbs have been administered to thousands of subjects in numerous clinical trials. Overall, they are well tolerated: A meta-analysis reviewing active and passive immunology compounds targeting Aβ, including several mAbs, found that there was no difference versus placebo on nearly all adverse events, serious adverse events, and deaths (Penninkilampi, Brothers et al. 2017). The one exception to the adverse event data was that subjects receiving anti-Aβ mAbs were more likely to experience amyloid-related imaging abnormalities (ARIA).

ARIA is the term that applies to cerebrovascular abnormalities detected via MRI. ARIA is classified into two categories: ARIA-E represents imaging findings related to vasogenic edema, sulcal effusions, and occasional gyral swelling, while ARIA-H captures MRI signal abnormalities reflective of parenchymal microhemorrhage and hemosiderin deposits (Sperling, Jack et al. 2011). Although both types have been documented in anti-Aβ mAb trials, ARIA-E occurs more frequently as a result of anti-Aβ mAb administration (Penninkilampi, Brothers et al. 2017, Greenberg, Bacskai et al. 2020). The exact mechanism(s) for ARIA is unknown, but it may be related to the clearance of amyloid from the cerebral vasculature or by provoking an inflammatory reaction at sites of vascular amyloid deposition (Greenberg, Bacskai et al. 2020). Risk factors for ARIA include administration of a mAb that targets the N-terminal of Aβ peptides; a previous history of microbleeds; carrying the ε4 allele of the apolipoprotein gene; and higher doses of drug, although it is unclear whether elevated ARIA risk is associated with absolute dose level or administration of higher doses without titration (van Dyck 2018, Aisen, Cummings et al. 2020, Greenberg, Bacskai et al. 2020).

5. SUMMARY OF THE INVENTION

AC-264713, also known as hu Aβ (AC-264713) [hu IgG1/K], is a recombinant humanized immunoglobulin G1 (IgG1) kappa monoclonal antibody (mAb) that binds to N-terminal truncated, pyroglutamate-modified at amino acid position 3, Aβ ($A\beta_{pE3}$), a particularly fast and insoluble aggregating form of Aβ. AC-264713 selectively binds to human $A\beta_{pE3\text{-}42}$ fibrils with a half maximal effective concentration ($EC_{50}$) of 0.7 nM and does not bind to nonpyroglutamated, full-length forms of A3.

Accordingly, the amino acid sequence for a recombinant humanized IgG1 kappa monoclonal antibody that specifically binds Aβ ($A\beta_{pE3}$) suitable to remove amyloid plaques from an AD brain is provided. The antibody structurally comprises a variable heavy and variable light chain including complementary determining regions (CDRs) that selectively binds to $A\beta_{pE3\text{-}42}$ fibrils. Also provided is an antibody including a heavy chain constant region including a fragment crystallizable region (Fc) and a light chain constant region. These structural elements, as encoded by the amino acid sequence of the antibody, provide a pharmaceutical composition effective at treating AD in a patient.

Described herein is an anti-human $A\beta_{pE3}$ antibody which comprises (i) a variable heavy chain (vH) comprising 3 CDRs; and (ii) a variable light chain (vL) comprising 3 CDRs, wherein:

```
vH CDR1 is
                              (SEQ ID NO: 1)
GFSLSTSGMGVS;

vH CDR2 is
                              (SEQ ID NO: 2)
HIYWDDDKRYNPYMKR;

vH CDR3 is
                              (SEQ ID NO: 3)
RADDYDVGFAY;
```

-continued vL CDR1 is
                                        (SEQ ID NO: 4)
LASQTIGTWLA;

vL CDR2 is
                                        (SEQ ID NO: 5)
AATSLAD;
and vL CDR3 is
                                        (SEQ ID NO: 6)
QQLYSSPFT.

In certain embodiments, the anti-human Aβ$_{pE3}$ antibody comprises a heavy chain variable region comprising the amino acid sequence set forth as SEQ ID NO:7 and a light chain variable region comprising the amino acid sequence set forth as SEQ ID NO:8.

In certain embodiments, the anti-human Aβ$_{pE3}$ antibody comprises two heavy chains, each heavy chain comprising the amino acid sequence set forth as SEQ ID NO:9, and two light chains, each light chain comprising the amino acid sequence set forth as SEQ ID NO:10.

In certain embodiments, the anti-human Aβ$_{pE3}$ antibody comprises an IgG constant region.

In certain embodiments, the anti-human Aβ$_{pE3}$ antibody comprises a human heavy chain constant region comprising an Fc portion, wherein the Fc portion is a human IgG1, IgG2, IgG3, IgG4, or IgM isotype.

In certain embodiments, the anti-human Aβ$_{pE3}$ antibody comprises a kappa light chain constant region.

Also provided herein are compositions comprising an anti-human Aβ$_{pE3}$ antibody which comprises (i) a variable heavy chain (vH) comprising 3 CDRs; and (ii) a variable light chain (vL) comprising 3 CDRs, wherein:

vH CDR1 is
                                        (SEQ ID NO: 1)
GFSLSTSGMGVS;

vH CDR2 is
                                        (SEQ ID NO: 2)
HIYWDDDKRYNPYMKR;

vH CDR3 is
                                        (SEQ ID NO: 3)
RADDYDVGFAY;

vL CDR1 is
                                        (SEQ ID NO: 4)
LASQTIGTWLA;

vL CDR2 is
                                        (SEQ ID NO: 5)
AATSLAD;
and vL CDR3 is
                                        (SEQ ID NO: 6)
QQLYSSPFT.

Also provided herein are methods for treating a neurodegenerative disorder comprising administering an anti-human Aβ$_{pE3}$ antibody which comprises (i) a variable heavy chain (vH) comprising 3 CDRs; and (ii) a variable light chain (vL) comprising 3 CDRs, wherein:

vH CDR1 is
                                        (SEQ ID NO: 1)
GFSLSTSGMGVS;

vH CDR2 is
                                        (SEQ ID NO: 2)
HIYWDDDKRYNPYMKR;

vH CDR3 is
                                        (SEQ ID NO: 3)
RADDYDVGFAY;

vL CDR1 is
                                        (SEQ ID NO: 4)
LASQTIGTWLA;

vL CDR2 is
                                        (SEQ ID NO: 5)
AATSLAD;
and vL CDR3 is
                                        (SEQ ID NO: 6)
QQLYSSPFT to a patient in need thereof.

In certain embodiments, the neurodegenerative disorder is Alzheimer's disease (AD).

Also provided herein is a polynucleotide comprising a nucleotide sequence encoding an anti-human Aβ$_{pE3}$ antibody, wherein the antibody comprises (i) a vH chain comprising three CDRs; and (ii) a vL chain comprising three CDRs, wherein:

vH CDR1 is
                                        (SEQ ID NO: 1)
GFSLSTSGMGVS;

vH CDR2 is
                                        (SEQ ID NO: 2)
HIYWDDDKRYNPYMKR;

vH CDR3 is
                                        (SEQ ID NO: 3)
RADDYDVGFAY;

vL CDR1 is
                                        (SEQ ID NO: 4)
LASQTIGTWLA;

vL CDR2 is
                                        (SEQ ID NO: 5)
AATSLAD;
and vL CDR3 is
                                        (SEQ ID NO: 6)
QQLYSSPFT.

Also provided herein is a vector comprising the polynucleotide comprising a nucleotide sequence encoding an anti-human Aβ$_{pE3}$ antibody, wherein the antibody comprises (i) a vH chain comprising three CDRs; and (ii) a vL chain comprising three CDRs, wherein:

(SEQ ID NO: 1)
vH CDR1 is GFSLSTSGMGVS;

(SEQ ID NO: 2)
vH CDR2 is HIYWDDDKRYNPYMKR;

(SEQ ID NO: 3)
vH CDR3 is RADDYDVGFAY;

(SEQ ID NO: 4)
vL CDR1 is LASQTIGTWLA;

-continued vL CDR2 is AATSLAD;
and
(SEQ ID NO: 5)

vL CDR3 is QQLYSSPFT.
(SEQ ID NO: 6)

Also provided herein is a eukaryotic host cell transformed with the vector comprising the polynucleotide comprising a nucleotide sequence encoding an anti-human $A\beta_{pE3}$ antibody, wherein the antibody comprises (i) a vH chain comprising three CDRs; and (ii) a vL chain comprising three CDRs, wherein:

vH CDR1 is GFSLSTSGMGVS;
(SEQ ID NO: 1)

vH CDR2 is HIYWDDDKRYNPYMKR;
(SEQ ID NO: 2)

vH CDR3 is RADDYDVGFAY;
(SEQ ID NO: 3)

vL CDR1 is LASQTIGTWLA;
(SEQ ID NO: 4)

vL CDR2 is AATSLAD;
and
(SEQ ID NO: 5)

vL CDR3 is QQLYSSPFT.
(SEQ ID NO: 6)

In certain embodiments, the eukaryotic host cell is a mammalian host cell.

Also provided herein is a method for producing an anti-human $A\beta_{pE3}$ antibody comprising: (a) culturing the mammalian host cell and (b) recovering the anti-human $A\beta_{pE3}$ antibody.

Further provided herein is an anti-human $A\beta_{pE3}$ antibody, wherein the antibody comprises two heavy chains, each heavy chain comprising the amino acid sequence set forth as SEQ ID NO: 37 and two light chains, each light chain comprising the amino acid sequence set forth as SEQ ID NO: 10.

6. BRIEF DESCRIPTION OF THE DRAWINGS

FIG. 1 shows representative binding of AC-264713 to human $A\beta_{pE3-42}$ fibrils. The binding of AC-264713 to human $A\beta_{pE3-42}$ fibrils was assessed in direct binding ELISA. Plates coated with human $A\beta_{pE3-42}$ fibrils (50 ng/well) were incubated with serially diluted AC-264713. The ELISA was repeated three times and a representative graph is shown. Plotted on the Y axis is Optical Density at 450 nm. The $EC_{50}$ value of AC-264713 binding to human $A\beta_{pE3-42}$ fibrils is 0.7 nM.

Figure 2:
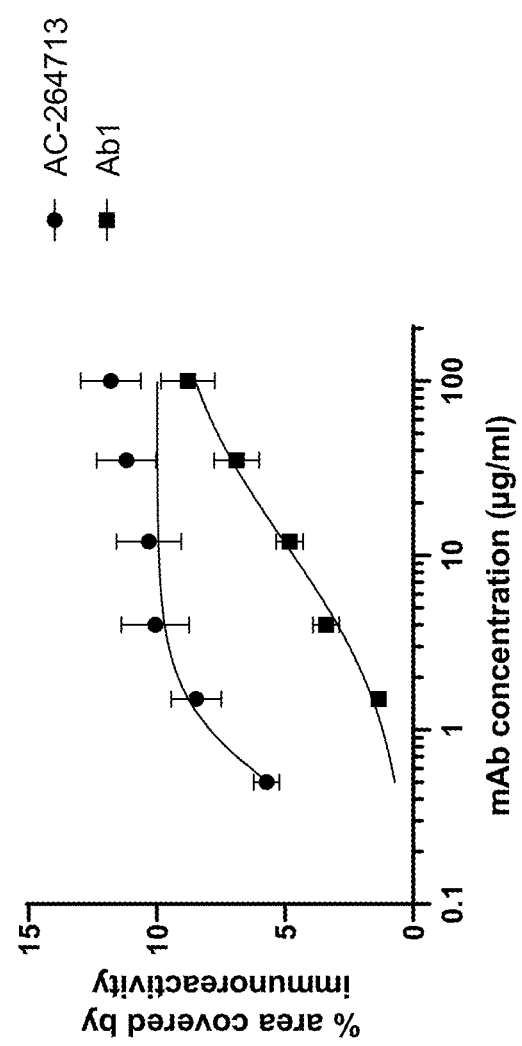

FIG. 2 depicts plaque area bound by AC-264713 and a comparator antibody Ab1 in fresh frozen human AD tissue from frontal cortex. Tissue from 6 AD donors were analyzed and the data were expressed as mean±SEM. AC-264713 bound plaques in AD brain tissue in a concentration-dependent manner. Lines represent fits to data for the 6 donors combined as described in Example 3.

Figure 3:
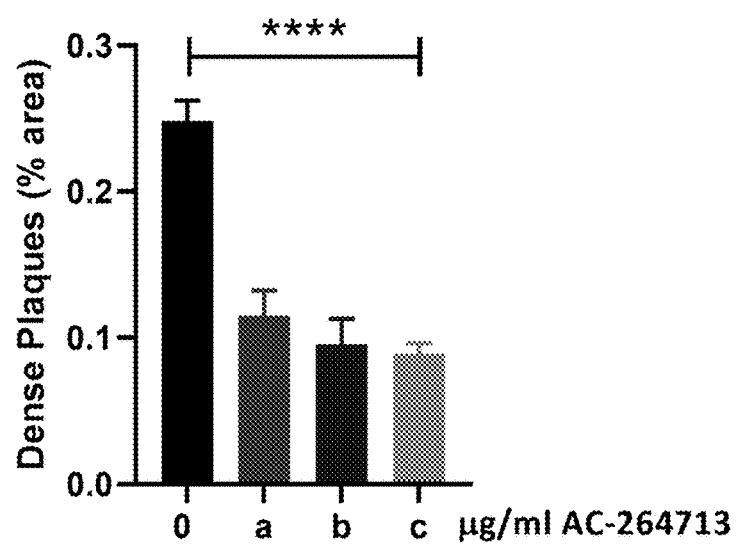

FIG. 3 shows that AC-264713 stimulates amyloid plaque removal from unfixed APPPS1-21 brain tissue by hiPSC-derived phagocytes. hiPSC-derived phagocytes were co-cultured with APPPS1-21 brain tissue pre-incubated with different concentrations of AC-264713. The amyloid plaques remaining in the tissue were stained using thioflavin S and quantified. Data were expressed as mean±SEM and analyzed with One-way ANOVA followed by Dunnett's multiple comparisons test *, p<0.05.

Figure 4:
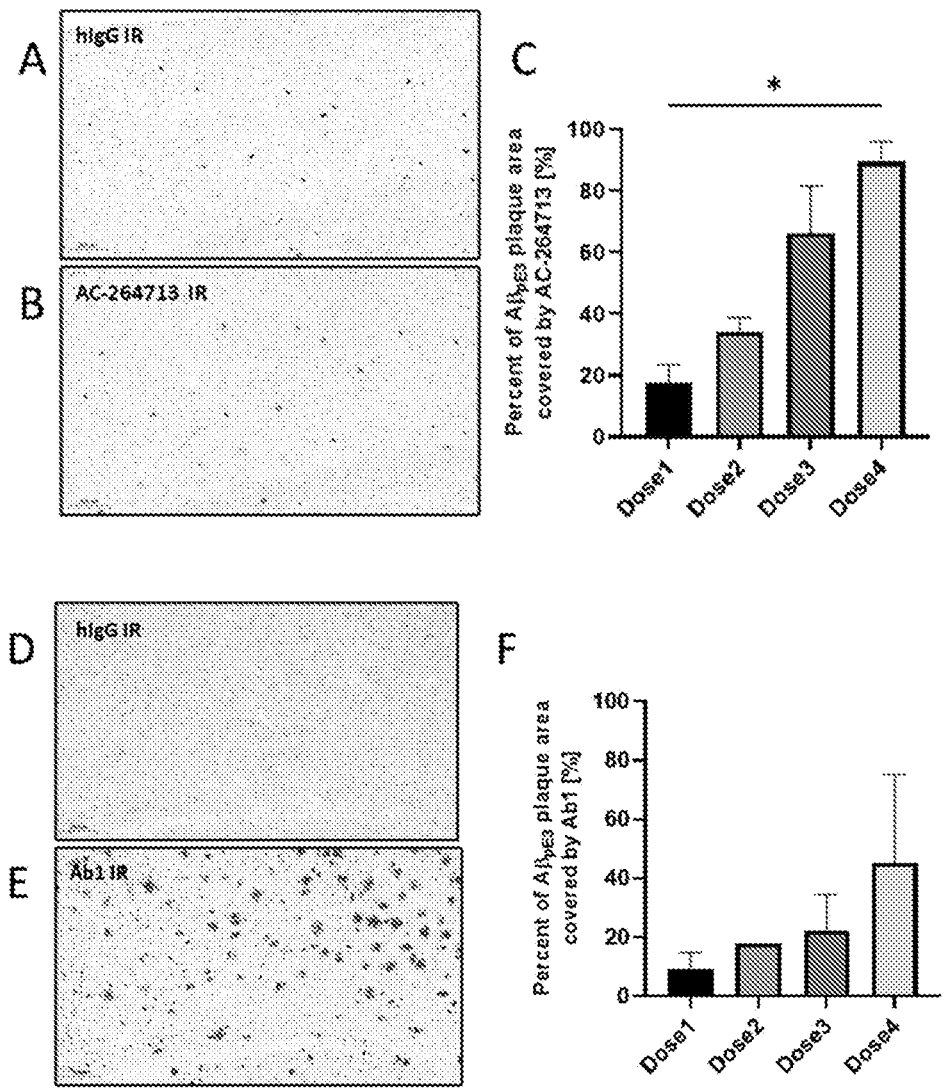

FIG. 4 depicts dose dependent target binding of AC-264713 in APPPS1-21 mice 72 hours following single intraperitoneal administration. AC-264713 (Panel A) and comparator antibody Ab1 (Panel D) in the brain were detected using anti-hIgG immunohistochemistry. The total target $A\beta_{pE3}$ on an adjacent section was stained using AC-264713 (Panel B) or comparator antibody Ab1 (Panel E). The % total target occupied by AC-264713 (Panel C) or comparator antibody Ab1 (Panel F) at increasing doses was then calculated and is presented on the y-axis. *P<0.05 (Kruskal-Wallis followed by Dunn's multiple comparison test).

Figure 5:
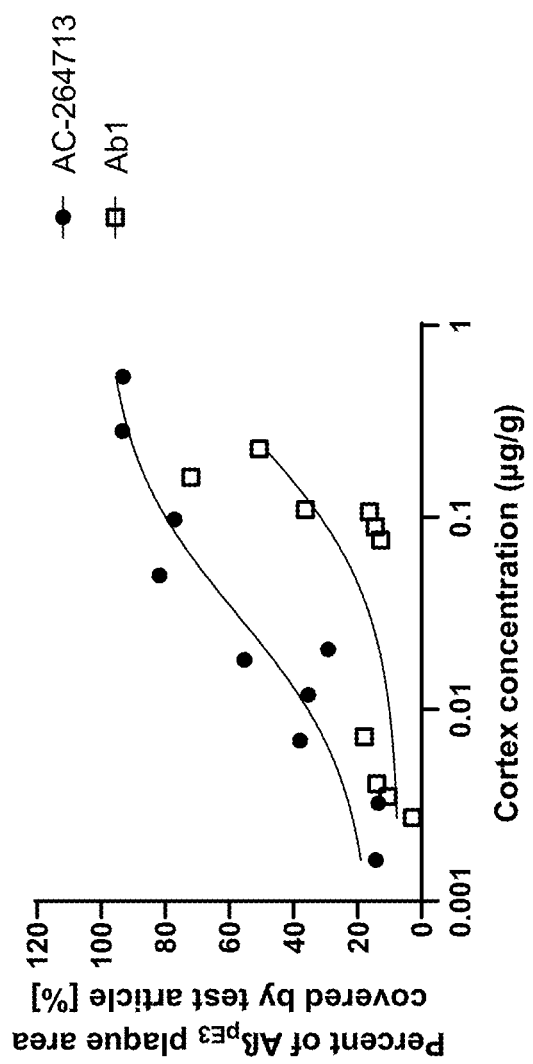

FIG. 5 shows the correlation of AC-264713 and comparator antibody Ab1 exposure in brain and dose-dependent target binding in APPPS1-21 mice 72 hours following single intravenous doses in female mice. Data (symbols) correlating individual animal brain exposure with $A\beta_{pE3}$ occupancy is shown together with the Nonlinear Fits (lines).

Figure 6:
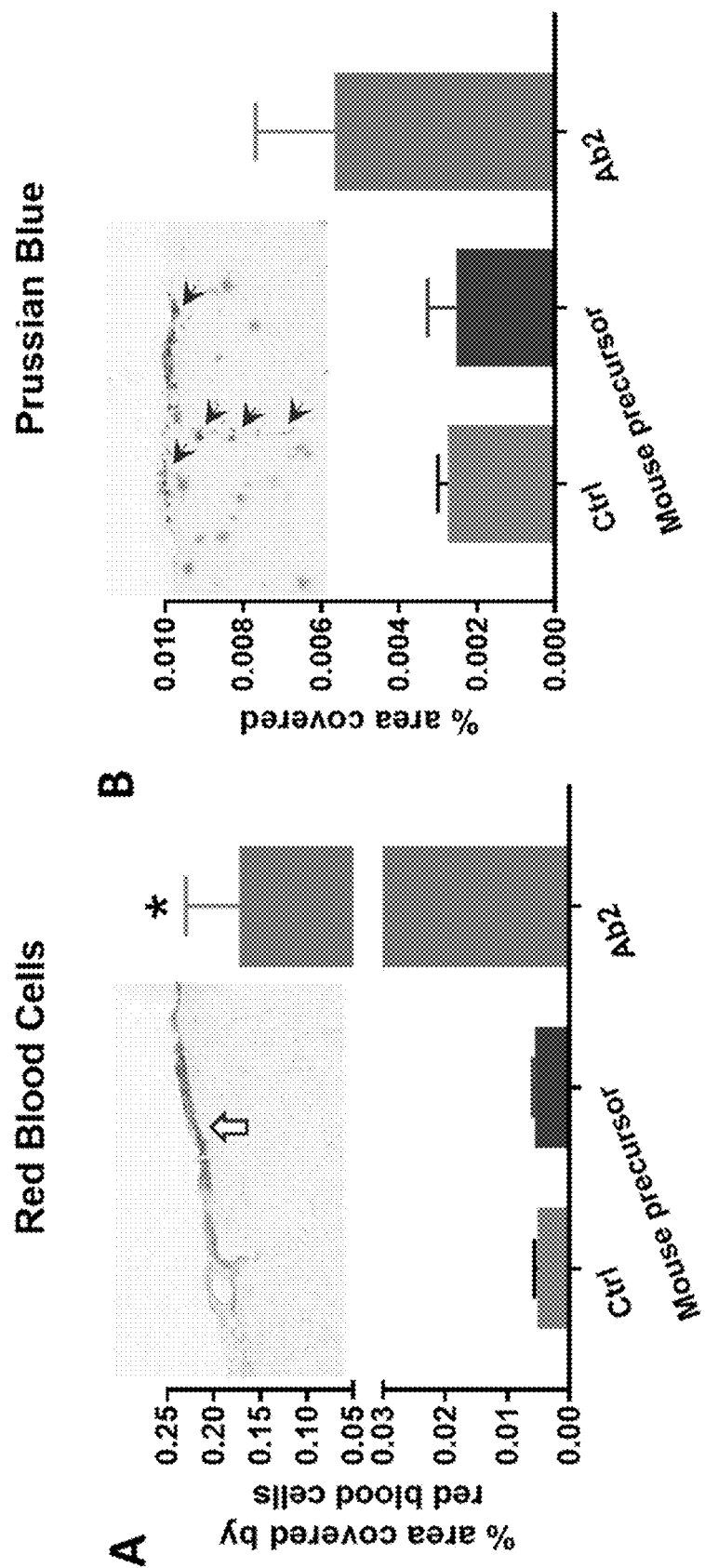

FIG. 6 shows the effects of AC-264713 on microhemorrhages in the APPPS1-21 mouse model which were studied using an AC-264713 mouse precursor antibody and a comparator antibody Ab2. (Panel A) Image of red blood cell quantification. (Panel B) Image of Prussian Blue quantification. Data were expressed as Mean±SEM. Staining images are representative of findings from positive control groups for microhemorrhage induction. Open arrow in Panel A indicates the red blood cells. Arrows in Panel B indicate the Prussian Blue staining signal.

7. DETAILED DESCRIPTION

For the purposes of promoting an understanding of the principles of the present disclosure, reference will now be made to various embodiments. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a," "an," and "the" are used herein to refer to one or to more than one (i.e., at least one) of the grammatical object of the article. By way of example, "an element" means at least one element and can include more than one element. The term "and/or" includes any and all combinations of one, or more, of the associated listed items and may be abbreviated as "/".

The term "comprise," as used herein, in addition to its regular meaning, may also include, and, in some embodiments, may specifically refer to the expressions "consist essentially of" and/or "consist of." Thus, the expression "comprise" can also refer to embodiments, wherein that which is claimed "comprises" specifically listed elements does not include further elements, as well as embodiments wherein that which is claimed "comprises" specifically listed elements may and/or does encompass further elements, or encompass further elements that do not materially affect the basic and novel characteristic(s) of that which is claimed. For example, that which is claimed, such as a method, kit, system, etc. "comprising" specifically listed elements also encompasses, for example, a method, kit, system, etc. "consisting of," i.e., wherein that which is claimed does not include further elements, and, for example, a method, kit, system, etc. "consisting essentially of," i.e., wherein that which is claimed may include further elements that do not materially affect the basic and novel characteristic(s) of that which is claimed.

"About," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which may encompass, for example, ±20%, ±15%, or ±10%, and in some embodiments, ±5%, ±3%, or ±2%, of the recited value and the range is included.

Unless otherwise defined, all technical terms used herein have the same meaning as commonly understood by one of ordinary skill in the art to which this disclosure belongs.

Embodiments of the disclosure relate to antibodies that bind to deposited forms of Aβ in the brain to stimulate an immune response that aids in clearing the protein, and methods of using these antibodies, for example, in the treatment of AD.

A$\beta_{pE3}$ is a form of Aβ that appears to be especially fast-aggregating (Jawhar, Wirths et al. 2011). Given that donanemab, which targets A$\beta_{pE3}$, achieved rapid plaque removal from human AD brain and A$\beta_{pE3}$ is less prevalent in the cerebral vasculature relative to other forms of Aβ (Kuo, Emmerling et al. 1997), anti-A$\beta_{pE3}$ antibodies, such as AC-264713, aiming to achieve rapid plaque removal with a lower risk for ARIA were generated.

AC-264713 is a recombinant humanized IgG1 kappa mAb that binds to A$\beta_{pE3}$. The origin of AC-264713 is a murine mAb that binds to A$\beta_{pE3}$. The variable domains of the murine antibody were humanized and then were fused with human IgG1 heavy chain and Ig kappa light constant regions to create AC-264713. It will be appreciated that humanizing, for example, a murine mAb, to provide a humanized mAb, such as the antibodies of the present disclosure, may be accomplished by any method known to one of skill in the art without limitation.

In some embodiments, the antibody of the disclosure comprises two variable chains, one heavy and one light. On each variable chain, there are three CDRs that allow the antibody to bind to A$\beta_{pE3}$. On the heavy and light variable chains, there are a combined total of six different CDRs. Additionally, in an embodiment the antibody contains a human heavy chain constant region including a human Fc of the immunoglobulin class G1 (IgG1). The anti-A$\beta_{pE3}$ antibodies described herein can be fucosylated or afucosylated and demonstrate in vitro functionality, immunosafety, and drug-like properties.

Antibodies according to the disclosure were generated via humanization and liability engineering of an antibody identified in a hybridoma campaign using the human A$\beta_{pE3-42}$ fibrils. To prioritize antibodies for humanization, the ability of antibodies to bind fibrillary A$\beta_{pE3-42}$ was evaluated. The anti-A$\beta_{pE3}$ antibody AC-264713 cross-reacts with human and cynomolgus A$\beta_{pE3}$, but does not bind mouse or rat A$\beta_{pE3}$.

As used herein, the term "antibody" (Ab) refers to an immunoglobulin molecule that specifically binds to a particular antigen, e.g., human A$\beta_{pE3}$ fibrils. The anti-A$\beta_{pE3}$ antibodies of the inventive concept bind to A$\beta_{pE3}$ and thereby modulate the immune system. Anti-A$\beta_{pE3}$ antibodies of the inventive concept include complementarity determining regions (CDRs), also known as hypervariable regions, in both the light chain and the heavy chain variable domains. The more highly conserved portions of variable domains are called the framework regions (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The inventive concept provides antibodies including modifications in these hybrid hypervariable positions. The variable domains of native heavy and light chains each include four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies. See Kabat et al., Sequences of Proteins of Immunological Interest (National Institute of Health, Bethesda, Md. 1987), which can be used to identify and number CDR sequences within a variable domain.

The antibodies of the disclosure may be monoclonal, genetically engineered, and/or otherwise modified in nature, including but not limited to chimeric antibodies, humanized antibodies, single chain antibodies, etc. In various embodiments, the antibodies include all or a portion of a constant region of an antibody. In some embodiments, the constant region is an isotype selected from: IgA (e.g., IgA1 or IgA2), IgD, IgE, IgG (e.g., IgG1, IgG2, IgG3 or IgG4), and IgM. In specific embodiments, the anti-A$\beta_{pE3}$ antibodies described herein include an IgG1. In other embodiments, the anti-A$\beta_{pE3}$ antibodies include an IgG2. In yet other embodiments, the anti-A$\beta_{pE3}$ antibodies include an IgG4. As used herein, the "constant region" of an antibody includes the natural constant region, allotypes or variants.

The light constant region of an anti-A$\beta_{pE3}$ antibody may be a kappa (κ) light region or a lambda (λ) region. A λ light region can be any one of the known subtypes, e.g., λ1, λ2, λ3, or λ4. In some embodiments, an anti-A$\beta_{pE3}$ antibody includes a kappa (κ) light region.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present inventive concept can be prepared using a wide variety of techniques known in the art including the use of hybridoma, recombinant, and phage display technologies, or a combination thereof.

The term "chimeric" antibody as used herein refers to an antibody having variable sequences derived from a non-human immunoglobulin, such as a rat or a mouse antibody, and human immunoglobulin constant regions, typically chosen from a human immunoglobulin template.

"Humanized" forms of non-human (e.g., murine) antibodies include substantially all of at least one, and typically two, variable domains, in which all or substantially all of the CDR regions correspond to those of a non-human immunoglobulin and all or substantially all of the FR regions are those of a human immunoglobulin sequence. The humanized antibody can also include at least a portion of an immunoglobulin constant region (Fc), typically that of a human immunoglobulin consensus sequence.

Anti-A$\beta_{pE3}$ antibodies of the disclosure include full-length (intact) antibody molecules comprising two full-length light chains and two full-length heavy chains.

Anti-Aβ$_{pE3}$ antibodies that include a human IgG4 constant region can include the S228P mutation, which has been reported to prevent Fab arm exchange. See, e.g., Silva, J P et al. Journal of Biological Chemistry, 290(9), 5462-5469 (2015).

Anti-Aβ$_{pE3}$ antibodies with high affinity for Aβ$_{pE3}$ may be desirable for therapeutic and diagnostic uses. Accordingly, the present inventive concept contemplates antibodies having a high binding affinity to Aβ$_{pE3}$. In specific embodiments, the anti-Aβ$_{pE3}$ antibodies bind to Aβ$_{pE3}$ with an affinity of at least about 25 nM, but may exhibit higher affinity, for example, at least about 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind human Aβ$_{pE3}$ with an affinity in the range of about 1 pM to about 10 nM, of about 100 pM to about 10 nM, about 100 pM to about 1 nM, about 100 pM to about 2 nM, or an affinity ranging between any of the foregoing values.

In some embodiments, the disclosure provides a monoclonal anti-Aβ$_{pE3}$ antibody with two full-length heavy chains and two full-length light chains, which comprise two sets of six different complementarity-determining regions (CDRs) within two sets of two different variable regions.

In some embodiments, the antibody is a recombinant, afucosylated, humanized, IgG1 kappa monoclonal antibody that binds to Aβ$_{pE3}$.

In an embodiment, the antibody comprises six CDRs including the following sequences:

```
                              (SEQ ID NO: 1)
vH CDR1 is GFSLSTSGMGVS;

(SEQ ID NO: 2)
vH CDR2 is HIYWDDDKRYNPYMKR;

(SEQ ID NO: 3)
vH CDR3 is RADDYDVGFAY;

(SEQ ID NO: 4)
vL CDR1 is LASQTIGTWLA;

(SEQ ID NO: 5)
vL CDR2 is AATSLAD;
and (SEQ ID NO: 6)
vL CDR3 is QQLYSSPFT.
```

In some embodiments, the antibody of the disclosure comprises a vH CDR1 including or having the amino acid sequence as set forth in SEQ ID NO:1, a vH CDR2 including or having the amino acid sequence as set forth in SEQ ID NO:2; a vH CDR3 including or having the amino acid sequence as set forth in SEQ ID NO:3, a vL CDR1 including or having the amino acid sequence as set forth in SEQ ID NO:4, a vL CDR2 including or having the amino acid sequence as set forth in SEQ ID NO:5; and a vL CDR3 including or having the amino acid sequence as set forth in SEQ ID NO:6.

In some embodiments, the antibody of the disclosure comprises a heavy chain variable region including or having the amino acid sequence as set forth in SEQ ID NO:7, or a sequence having at least 98% sequence identity to SEQ ID NO:7:

```
                                       (SEQ ID NO: 7)
EVQLQESGPGLVKPSQTLSLTCTFSGFSLSTSGMGVSWIRQPPGKGLEW

LAHIYWDDDKRYNPYMKRRLTISKDTSKNQVSLKISSVTAADTAVYYCA

RRADDYDVGFAYWGQGTLVTVSS
```

In some embodiments, the antibody of the disclosure comprises a light chain variable region including or having the amino acid sequence as set forth in SEQ ID NO:8, or a sequence having at least 98% sequence identity to SEQ ID NO:8:

```
                                       (SEQ ID NO: 8)
DIQMTQSPSSVSASVGDRVTITCLASQTIGTWLAWYQQKPGKSPKLLIY

AATSLADGVPSRFSGSGSGTDFTLTISSLQPEDFATYYCQQLYSSPFTF

GQGTKLEIK
```

In some embodiments, the antibody of the disclosure comprises a heavy chain including or having the amino acid sequence as set forth in SEQ ID NO:9, or a sequence having at least 98% sequence identity to SEQ ID NO:9 (constant region is bold; the variable heavy domain is underlined; CDRs are *underlined bold italic* (as set forth in SEQ ID NOS:1-3, respectively, in order of appearance)):

```
                                       (SEQ ID NO: 9)
EVQLQESGPGLVKPSQTLSLTCTFS***GFSLSTSGMGVS***WIRQPPGKGLE

WLA***HIYWDDDKRYNPYMKR***RLTISKDTSKNQVSLKISSVTAADTAVYY

CAR***RADDYDVGFAY***WGQGTLVTVSSASTKGPSVFPLAPSSKSTSGGTA

ALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVM

HEALHNHYTQKSLSLSPGK.
```

In some embodiments, the antibody of the disclosure includes a heavy chain having the C-terminal lysine truncated, for example, a heavy chain as set forth in SEQ ID NO:9, with the C-terminal lysine truncated/removed.

In some embodiments, the antibody of the disclosure comprises a light chain including or having the amino acid sequence as set forth in SEQ ID NO:10, or a sequence having at least 98% sequence identity to SEQ ID NO:10 (constant region is bold; the variable heavy domain is underlined; CDRs are *underlined bold italic* (as set forth in SEQ ID NOS:4-6, respectively, in order of appearance)):

```
                                      (SEQ ID NO: 10)
DIQMTQSPSSVSASVGDRVTITC***LASQTIGTWLA***WYQQKPGKSPKLLIY

*AATSLAD*GVPSRFSGSGSGTDFTLTISSLQPEDFATYYC*QQLYSSPFT*F

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.
```

Embodiments of the inventive concept also include nucleic acids that encode the heavy chain sequences of SEQ ID NO:9, and nucleic acids that encode the light chain sequence of SEQ ID NO:10. In some embodiments, for example, the mature heavy chain sequence as set forth in SEQ ID NO:9 may be encoded by the nucleic acid sequence set forth in SEQ ID NO:13 (the constant region is encoded by the sequences in bold; the variable heavy domain is encoded by the sequences that are underlined; and the CDRs are encoded by sequences are *underlined bold italic*):

(SEQ ID NO: 13)
GAAGTGCAGCTGCAAGAGTCCGGCCCGGGCTTGGTCAAGCCGTCGCAG

ACCCTCAGCCTTACTTGCACCTTCTCG<u>GGATTCTCGCTGT</u>

<u>*CCACTAGCGGCATGGGCGTGTCG*</u>TGG ATCAGGCAGCCTCCTGGCAAA

GGGCTGGAGTGGCTTGCC <u>*CACATCTACTGGGACGAT*</u>

<u>*GACAAGAGATACAACCCCTATATGAAGCGC*</u> CGCCTGACCATCAGCAA

GGACACCTCCAAAAACCAAGTCTCGCTGAAGATCTCCTCCGTGACCGC

CGCGGATACCGCCGTGTACTACTGCGCCCGG <u>*CGGGCCGACGA*</u>

<u>*CTATGACGTGGGATTTGCGTAC*</u> TGGGGACAGGGGACCCTGGTCACCG

TGTCCTCCGCCTCAACTAAGGGACCCAGCGTGTTCCCTCTCGCCCCAT

CATCGAAGTCCACTAGTGGCGGGACCGCTGCTCTCGGTTGTCTGGTTA

AGGACTACTTCCCGGAACCCGTCACCGTATCATGGAACTCCGGTGCAC

TGACATCCGGCGTGCACACCTTCCCGGCCGTGCTGCAAAGCTCCGGAC

TGTACTCCCTGTCGAGCGTGGTCACTGTGCCCTCATCAAGCCTGGGTA

CTCAGACGTACATTTGCAACGTGAACCACAAGCCGTCCAACACCAAGG

TCGACAAGAAAGTGGAGCCGAAGTCCTGCGACAAGACCCATACTTGCC

CGCCGTGCCCAGCCCCTGAGCTGCTGGGTGGACCGAGCGTGTTCCTGT

TCCCACCTAAACCCAAGGACACCCTGATGATTAGCCGCACCCCCGAAG

TGACCTGTGTGGTCGTGGATGTGTCCCACGAAGATCCCGAAGTCAAGT

TCAATTGGTACGTGGACGGCGTCGAAGTGCATAACGCCAAGACTAAGC

CCCGCGAGGAACAGTACAACAGCACCTACCGGGTGGTGTCCGTGCTCA

CTGTCCTGCACCAAGACTGGCTGAACGGAAAGGAGTACAAGTGCAAAG

TGTCCAACAAGGCACTGCCAGCGCCCATCGAGAAAACGATCAGCAAGG

CCAAGGGCCAGCCGAGAGAACCTCAGGTCTACACCCTGCCGCCATCCC

GGGAAGAAATGACCAAGAACCAAGTGTCCCTTACCTGTCTCGTGAAGG

GATTCTACCCTTCCGACATCGCCGTGGAGTGGGAGTCCAATGGACAGC

CGGAGAACAACTACAAGACTACCCCTCCTGTGCTGGACTCCGATGGAT

CTTTCTTCCTGTACTCGAAGCTCACCGTGGATAAGTCGCGGTGGCAAC

AGGGGAATGTGTTCAGCTGCTCCGTGATGCACGAAGCTCTGCATAACC

ACTACACTCAGAAGTCGCTGTCACTCTCCCCCGGGAAA

In some embodiments, for example, the mature light chain sequence as set forth in SEQ ID NO:10 may be encoded by the nucleic acid sequence set forth in SEQ ID NO: 14 (the constant region is encoded by the sequences in bold; the variable light domain is encoded by the sequences that are underlined; and the CDRs are encoded by sequences are underlined bold *underlined bold* *italic*):

(SEQ ID NO: 14)
GACATCCAGATGACCCAGTCCCCGTCCTCGGTGTCAGCGTCAGTGGGG

GACAGGGTCACGATCACTTGC <u>*CTGGCCAGCCAGACCA*</u>

<u>*TTGGCACTTGGCTGGCC*</u> TGGTATCAGCAGAAGCCCGGAAAGTCACCG

AAGCTGTTGATCTAC <u>*GCCGCAACTTCCCTGGCCGAT*</u> GGCGTGCCCT

CGCGGTTCTCCGGTTCCGGGTCGGGAACTGACTTTACCCTGACCATTA

GCTCTCTGCAACCTGAGGACTTCGCCACCTACTACTGT

<u>*CAGCAACTGTACTCCTCGCCGTTCACC*</u> TTCGGACAAGGCACCAAGT

TGGAAATCAAGCGGACTGTGGCGGCACCCAGCGTGTTCATCTTTCCTC

CATCCGACGAACAGCTGAAGTCCGGTACCGCTAGCGTGGTCTGTCTCC

TGAACAACTTCTACCCGCGCGAGGCCAAGGTCCAGTGGAAGGTCGACA

ACGCGCTCCAGAGCGGCAACAGTCAGGAATCCGTGACCGAACAGGACT

CCAAGGATTCGACCTACTCGCTGTCCTCCACTCTCACCCTGTCCAAAG

CCGATTACGAGAAGCACAAAGTGTACGCTTGCGAAGTGACCCATCAAG

GCCTTAGCAGCCCCGTGACAAAGTCCTTCAATCGGGGAGAGTGC

It will be appreciated by one of skill in the art that, as a result of codon degeneracy in the genetic code, nucleic acid sequences that differ from the sequences as set forth in SEQ ID NOS:13, 14, 15, and 16, encoding the heavy chain sequence of SEQ ID NO:9, the light chain sequence of the of SEQ ID NO:10, the heavy chain sequence of SEQ ID NO:11 and the light chain sequence of the of SEQ ID NO:12 respectively, are contemplated without departing from the scope of the inventive concept.

In some embodiments, the antibody comprises a human heavy chain constant region including human CH1, human hinge, human CH2, and human CH3 domain. In some embodiments, the encoded heavy chain constant region comprises an Fc portion, wherein the Fc portion is a human IgG1, IgG2, IgG3, IgG4, or IgM isotype. In an embodiment, the Fc is an IgG1, and the allotype is z, non-a. In an embodiment, the light chain is a kappa light chain.

Polynucleotides Encoding the Anti-A$\beta_{pE3}$ Antibodies, Expression Systems and Methods of Making the Antibodies The present inventive concept encompasses polynucleotide molecules encoding immunoglobulin light and heavy chain genes for anti-A$\beta_{pE3}$ antibodies, vectors including such polynucleotides, and host cells capable of producing the anti-A$\beta_{pE3}$ antibodies of the disclosure.

An anti-A$\beta_{pE3}$ antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered.

To generate polynucleotides encoding such anti-A$\beta_{pE3}$ antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR)

Once DNA fragments encoding anti-A$\beta_{pE3}$ antibody-related VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2, CH3 and, optionally, CH4). The sequences of human heavy chain constant region genes are known in the art (See, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but in certain embodiments is an IgG1 or IgG4. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (See, e.g., Kabat, et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region.

To express the anti-$A\beta_{pE3}$ antibodies, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-$A\beta_{pE3}$ antibody-related light or heavy chain sequences, the expression vector can already carry antibody constant region sequences. For example, one approach to converting the anti-$A\beta_{pE3}$ monoclonal antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced. For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR-CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-$A\beta_{pE3}$ antibody of the disclosure.

Recombinant DNA technology can also be used to remove some or all of the DNA encoding either or both of the light and heavy chains that is not necessary for binding to $A\beta_{pE3}$. The molecules expressed from such truncated DNA molecules are also encompassed by the antibodies of the disclosure.

For recombinant expression of an anti-$A\beta_{pE3}$ antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a polynucleotide encoding one or more portions of an anti-A$\beta_{pE3}$ antibody has been obtained, further alterations or mutations can be introduced into the coding sequence, for example to generate polynucleotides encoding antibodies with different CDR sequences, antibodies with reduced affinity to the Fc receptor, e.g., antibodies with LALA mutations, or antibodies of different subclasses. It will be appreciated that further alterations and/or mutations can be introduced into the coding sequence to generate polynucleotides encoding antibodies may be accomplished by any method known to one of skill in the art without limitation, and the polynucleotides generated used to produce, for example, further anti-A$\beta_{pE3}$ antibodies, such as anti-A$\beta_{pE3}$ antibodies with reduced affinity to the Fc receptor, and/or anti-A$\beta_{pE3}$ antibodies of different subclasses.

The anti-A$\beta_{pE3}$ antibodies of the disclosure can also be produced by chemical synthesis or by using a cell-free platform.

Purification of Anti-A$\beta_{pE3}$ Antibodies

Once a polypeptide of the disclosure has been produced by recombinant expression, it can be purified by any method known in the art for purification of a protein.

Once isolated, an anti-A$\beta_{pE3}$ antibody can be further purified.

Compositions

The antibodies of this disclosure may be provided as a composition suitable for administration to a subject. In some embodiments, the antibody composition is a pharmaceutical composition, including an antibody of this disclosure and a pharmaceutically acceptable carrier.

Summary of Properties of Subject Antibodies

Properties of subject antibodies, exemplified by but not limited to AC-264713, include the following:

High affinity binding to human A$\beta_{pE3}$ fibrils, e.g., EC$_{50}$ for human A$\beta_{pE3-42}$ fibrils as determined in, for example, by the direct binding ELISA of Example 1 of about 2.5 nM or lower, 2 nM or lower, 1.5 nM or lower, 1 nM or lower, 0.9 nM or lower, 0.8 nM or lower, 0.7 nM or lower, 0.6 nM or lower, about 0.5 nM or lower, 0.4 nM or lower, about 0.3 nM or lower, about 0.2 nM or lower, about 0.1 nM or lower, or about 0.05 nM or lower, or any range of values for EC$_{50}$ between about 0.05 nM and about 2.5 nM.

High specificity binding to human A$\beta_{pE3}$ fibrils, e.g., no significant cross-reacting with human A$\beta_{pE11-40}$ fibrils, and no significant cross reacting with A$\beta_{1-40}$ from all species, including human, monkey, dog, rabbit, rat, and mouse.

Good immunosafety determined by cytokine release assay.

In some embodiments, the antibodies of the disclosure may, for example, exhibit binding to AD brains that contain amyloid plaques in a dose-dependent manner with an EC$_{50}$ of 0.4 µg/mL, while not binding to non-AD human, rat, or cynomolgus monkey brain tissue where amyloid plaques are not present.

Data from a study using an APPPS1-21 mouse model that expresses human transgenes for amyloid precursor protein and presenilin 1 indicated that AC-264713 enters the brain and binds to A$\beta$ plaques after a single injection. AC-264713 also binds to amyloid plaques in human brain tissue from donors with AD. Additionally, in vitro data demonstrated that the fragment crystallizable (Fc) portion of AC-264713 has full effector function to trigger plaque removal mediated via hiPSC-derived phagocytes. When evaluated in an acute microhemorrhage model using APPPS1-21 mice, AC-264713 did not induce microhemorrhage. Taken together, the data support that AC-264713, i.e., an anti-human A$\beta_{pE3}$ fibril monoclonal antibody with full effector function removes amyloid plaques from an AD brain.

Methods of Use

In embodiments, the methods described herein involve treating patients who have AD with the anti-A$\beta_{pE3}$ antibodies of the disclosure.

"Inhibiting", "reducing," or any variation of these terms in relation to, e.g., treating AD and the development of A$\beta$ plaques related to AD includes any measurable decrease or complete inhibition to achieve a desired result. For example, there may be a decrease (removal) of about, at most about, or at least about 5%, 10%, 15%, 20%, 25%, 30%, 35%, 40%, 45%, 50%, 55%, 60%, 65%, 70%, 75%, 80%, 85%, 90%, 95%, 99% of A$\beta$ plaque load, or more, or any range derivable therein, or reduction in development of A$\beta$ plaques in, and the treatment of, a patient with AD.

8. EXAMPLES

The following examples, which highlight certain features and properties of the exemplary embodiments of the inventive concept described herein are provided for purpose of illustration.

Example 1: Panel of Identified Recombinant Hybridoma mAbs Binding to Recombinant A$\beta$ Proteins Direct binding ELISA was employed to assess the ability of identified and recombinantly expressed panel of mAbs for binding to human A$\beta_{pE3-42}$ fibrils and their cross-reactivity to human A$\beta_{1-40}$, human A$\beta_{1-42}$ or human A$\beta_{pE11-40}$. Due to 100% sequence identity between human, monkey, dog, and rabbit; binding studies were done with human A$\beta_{1-40}$ and A$\beta_{1-42}$ as representative for these other species. Recombinant human A$\beta$ proteins were diluted in 0.2 M carbonate-bicarbonate buffer. A$\beta$ proteins were diluted from 0.1 mM/0.2 mM stock solution to a working concentration of 1 µg/mL, and 50 µL per well (50 ng/well) was added to 96-well half area high-binding ELISA plates. The plates were incubated overnight at 4° C. shaking at 100 rpm. Following coating, the plates were washed four times with 190 µL/well of 1×PBS using an automated plate washer. The plates were blocked with 190 µL/well of 2% BSA in DPBS and incubated for 1 hr. at room temperature (RT). Reagents for ELISA were diluted in 0.25% BSA in DPBS.

| List of A$\beta$ peptides tested in ELISA | | |
|---|---|---|
| Peptide Sequence | Sequence | |
| A$\beta_{pE3-42}$ fibrils | (Pyr-E)FRHDSGYEV HHQKLVFFAE DVGSNKGAII GLMVGGVVIA | SEQ ID NO: 17 |
| A$\beta_{pE11-40}$ fibrils | (Pyr-E)VHHQKLVFF AEDVGSNKGA IIGLMVGGVV | SEQ ID NO: 18 |
| A$\beta$ 3-42 monomer | EFRHDSGYEV HHQKLVFFAE DVGSNKGAII GLMVGGVVIA | SEQ ID NO: 19 |
| A$\beta$ 3-42 fibrils | EFRHDSGYEV HHQKLVFFAE DVGSNKGAII GLMVGGVVIA | SEQ ID NO: 19 |

List of Aβ peptides tested in ELISA

| Peptide Sequence | Sequence | |
|---|---|---|
| Aβ 1-40 fibrils | DAEFRHDSGY EVHHQKLVFF AEDVGSNKGA IIGLMVGGVV | SEQ ID NO: 20 |
| Aβ 1-42 fibrils | DAEFRHDSGY EVHHQKLVFF AEDVGSNKGA IIGLMVGGVV | SEQ ID NO: 21 |
| Mouse/Rat Aβ 1-40 | DAEFGHDSGF EVRHQKLVFF AEDVGSNKGA IIGLMVGGVV | SEQ ID NO: 22 |

Dilutions for the panel of mAbs were prepared in dilution plates from stock solutions to a working 1× initial concentration of either 67 nM or 100 nM, and an 8-point 5× dilution series for each mAb was performed. After incubation for blocking, plates were washed four times with 190 µL/well of 1×PBS using automated plate washer. Anti-mouse IgG-HRP at a 1:10,000 dilution was prepared for detection and 50 µL was added to each well. The plates were incubated for 30 min at RT. After four washes with 1×PBS, 50 µL of TMB substrate (Life Technology, 002023) was added into each well, and the plates were incubated at RT for about 5-10 min until color developed. The reaction was stopped by adding 50 µL per well of 2N sulfuric acid. Plates were read on a plate reader to obtain the absorbance at 450 nm ($OD_{450}$). Binding ($EC_{50}$) of mAbs to Aβ proteins was calculated using nonlinear regression (4-parameter dose-response curve model: Y=Bottom+(TopBottom)/(1+10^((Log IC50-X)*Hillslope))) in GraphPad Prism 8.4.3.

Monoclonal antibody (mAb) AC-233661 showed specificity and selectivity for the $Aβ_{pE3-42}$ species and was selected for humanization. AC-264713 is the humanized version of AC-233661.

In some cases, AC-264713 is characterized using a comparator antibody. Amino acid sequences for antibodies included in experiments for comparison purposes are described below:

| Antibody | | |
|---|---|---|
| Comparator Ab1 | Heavy Chain | SEQ ID NO: 23 |
| | Light Chain | SEQ ID NO: 24 |
| Comparator Ab2 | Heavy Chain | SEQ ID NO: 25 |
| | Light Chain | SEQ ID NO: 26 |
| Mouse precursor antibody (AC-233661) | Heavy Chain | SEQ ID NO: 11 |
| | Light Chain | SEQ ID NO: 12 |

Example 2: Binding Specificity and Epitope Identification

A. Binding Specificity to Human $Aβ_{pE3-42}$ Fibrils

Binding of AC-264713 against human $Aβ_{pE3-42}$ fibrils was assessed using the methods as described in Example 1, except that anti-human IgG-HRP was used for detection instead of anti-mouse IgG-HRP. The $EC_{50}$ value for binding of AC-264713 against human $Aβ_{pE3-42}$ fibrils is 0.7 nM. FIG. 1 shows representative binding of AC-264713 to human $Aβ_{pE3-42}$ fibrils.

B. Epitope Identification

Ten biotinylated peptides from N-terminal 3-16 amino acid length with glycine point positional changes substituting each amino acid starting from amino acid three were generated with biotin at the C-terminus as listed below.

List of glycine positional mutated Aβ peptides

| Peptide Sequence | SEQ ID NO: |
|---|---|
| pE3-16 Pyr-EFRHDSGYEVHHQK-Biotin | SEQ ID NO: 27 |
| 4-16-FRHDSGYEVHHQK-Biotin | SEQ ID NO: 28 |
| 5-16-RHDSGYEVHHQK-Biotin | SEQ ID NO: 29 |
| E3-16-EFRHDSGYEVHHQK-Biotin | SEQ ID NO: 30 |
| pEG4 Pyr-EGRHDSGYEVHHQK-Biotin | SEQ ID NO: 31 |
| mpE3 16-Pyr-EFGHDSGFEVHHQK-Biotin | SEQ ID NO: 32 |
| pEG6 Pyr EFRGDSGYEVHHQK-Biotin | SEQ ID NO: 33 |
| pEG7 Pyr EFRHGSGYEVHHQK-Biotin | SEQ ID NO: 34 |
| pEG8 Pyr EFRHDGGYEVHHQK-Biotin | SEQ ID NO: 35 |
| pEF10 Pyr EFRHDSGGVHHQK-Biotin | SEQ ID NO: 36 |

Aβ = amyloid-beta; The amino acids mutated to glycine are highlighted and bolded and underlined The ability of AC-264713 to bind to the peptides was assessed by direct binding ELISA. Loss in binding indicates that the residue is required by AC-264713 to bind $Aβ_{pE3-42}$ fibrils. Recombinant human Aβ biotinylated peptides were diluted in distilled water. Aβ peptides were diluted to a working concentration of 2 µg/mL, and 50 µL per well (100 ng/well) was added to 96-well half area high-binding ELISA plates. The plates were incubated overnight at 4° C. shaking at 100 rpm. Following coating, the plates were washed four times with 190 µL/well of 1×PBS using an automated plate washer. The plates were blocked with 190 µL/well of 2% BSA in DPBS and incubated for 1 hr. at RT. Reagents for ELISA were diluted in 0.25% BSA in DPBS.

Dilutions for AC-264713 were prepared in dilution plates from stock solutions to a working 1× initial concentration of either 67 or 100 nM, and an 8-point 5× dilution series for mAb was performed. After incubation for blocking, plates were washed four times with 190 µL/well of 1×PBS using automated plate washer. Anti-human IgG-HRP at a 1:10,000 dilution was prepared for AC-264713 detection and 50 µL was added to each well. The plates were incubated for 30 min at RT. After four washes with PBS, 50 µL of TMB substrate was added into each well, and the plates were incubated at RT for about 5-10 min until color developed. The reaction was stopped by adding 50 µL per well of 2N sulfuric acid. Plates were read on a ClarioStar plate reader to obtain the absorbance at 450 nm ($OD_{450}$). Binding ($EC_{50}$) of AC-264713 to Aβ proteins was calculated using nonlinear regression (4-parameter dose-response curve model: Y=Bottom+(TopBottom)/(1+10^((Log IC50-X)*Hillslope))) in GraphPad Prism 8.4.3. Three independent experiments were performed.

The results are summarized in the table below.

| Epitope Finder ELISA $EC_{50}$ Values - Glycine Positional Mutated Aβ Peptide Binding $EC_{50}$ Values for AC-264713 | |
|---|---|
| Peptide (SEQ ID NO:) | $EC_{50}$ (nM) (average ± SD) |
| pE3-16 (SEQ ID NO: 27) | 0.3 ± 0.1 |
| 4-16 (SEQ ID NO: 28) | NB |

-continued

Epitope Finder ELISA $EC_{50}$ Values - Glycine Positional Mutated Aβ Peptide Binding $EC_{50}$ Values for AC-264713

| Peptide (SEQ ID NO:) | $EC_{50}$ (nM) (average ± SD) |
|---|---|
| 5-16 (SEQ ID NO: 29) | NB |
| E3-16 (SEQ ID NO: 30) | 0.9 ± 0.1 |
| pEG4 (SEQ ID NO: 31) | NB |
| mpE3-16 (SEQ ID NO: 32) | NB |
| pEG6 (SEQ ID NO: 33) | 0.5 ± 0.1 |
| pEG7 (SEQ ID NO: 34) | 0.4 ± 0.1 |
| pEG8 Pyr (SEQ ID NO: 35) | 0.4 ± 0.03 |
| pEF10 (SEQ ID NO: 36) | 0.5 ± 0.1 |

Binding analysis of AC-264713 to glycine mutant peptides indicates the residues pyro 3, 4 and 5 are important for binding. Interestingly, AC-264713 binds to E3-16 but with 3-fold reduced binding potency as compared to pE3-16, which could be due to spontaneous conversion of glutamate to pyroglutamate in the recombinant Aβ peptide preparation.

Example 3 Binding of AC-264713 to Amyloid Plaques in AD Brain Tissue

Unfixed, 20 μm tissue sections were prepared from cerebral cortex of human cadaver AD brain using a cryostat and were thaw-mounted onto glass slides. The tissue sections were then incubated in Tris-buffered saline (TBS) containing 0.3% $H_2O_2$ for 10 minutes. After three washes with TBS, the sections were incubated in TBS containing 3% milk for 30 minutes. Then biotinylated AC-264713 was added to the samples and incubated at 4° C. overnight. After three washes with TBS, the immunoreactivity was visualized by incubation in 1:400 ABC Elite for one hour followed by DAB for five minutes.

The images were acquired from all the samples using a slide scanner. The IR of biotinylated AC-264713 in the AD samples (n=6) were quantified using the Area Quantification module in HALO™ image analysis software v3.1.1076.423. Using the software, the gray matter was outlined, and the "threshold" was determined by an observer who was blind to the staining conditions. The threshold was set so that the DAB signal was recognized by the software and the background/non-specific staining was excluded from the analysis. Once an appropriate threshold was set, the software measured the percentage of the area of interest containing the positive signal.

A nonlinear regression analysis was carried out using Prism Version 9.1.0 (Graph Pad Software). A variable slope model, % area covered by IR=Bottom+$(X^{HillSlope})$*(Top−Bottom)/$(X^{HillSlope}+EC_{50}^{HillSlope})$, was used, where Bottom was fixed to zero, and Top was fixed to 10% as the typical total area covered by plaques. Data for all six donors were analyzed in a combined data fit.

In AD brain tissue (n=6), AC-264713 binds the plaques in a concentration-dependent manner in the range of 0.5-100 μg/mL (FIG. 2) with an $EC_{50}$ of 0.4 μg/ml (confidence interval: 0.1-0.7 μg/ml). For comparison, $EC_{50}$ for comparator antibody Ab1 binding to AD brain tissue was estimated to be 12 μg/ml (FIG. 2. confidence interval: 8-17 μg/ml). Hill coefficients for both, AC-264713 and Ab1 were close to 1 (1.5 and 0.8, respectively).

FIG. 2 depicts plaque area bound by AC-264713 and a comparator antibody Ab1 in fresh frozen human AD tissue from frontal cortex.

Example 4 Stimulated Amyloid Plaque Removal from Unfixed APPPS1-21 Brain Tissue by hiPSC-derived Phagocytes Assay Protocol Unfixed, 20 m coronal brain tissue sections were prepared from 21 months old APPPS1-21 mice on a cryostat and were thaw-mounted onto 12 mm poly-D-lysine-coated glass coverslips. Dried tissue sections were washed briefly with PBS and incubated overnight with 0, or with dose a, dose b or dose c (wherein 0 μg/ml<dose a<dose b<dose c) of AC-264713 in PBS at 4° C. Immediately before addition of human induced pluripotent stem cell (hiPSC)-derived phagocytes, tissue sections were washed three times with PBS.

hiPSC-derived phagocytes were generated as described previously (van Wilgenburg, Browne et al. 2013, Haenseler, Sansom et al. 2017). Briefly, dissociated hiPSCs were aggregated into hematopoietic embryoid bodies (EBs) in EB differentiation medium [mTeSR-1 supplemented with Revitacell, 50 ng/ml human VEGF, 50 ng/ml human BMP-4 (Peprotech), and 20 ng/ml SCF (R&D Systems)]. EBs were maintained in T75 culture flasks containing EB maintenancemedium [X-VIVO 15 supplemented with 100 U/ml penicillin, 100 μg/ml streptomycin (Thermo-Fisher), 2 mM Glutamax, 55 μM 2-mercaptoethanol, 100 ng/mL recombinant human M-CSF, and 25 ng/mL recombinant human IL-3]. Phagocyte suspensions were harvested from EB flasks and cultured directly onto antibody-treated APPPS1-21 tissue sections at a density of 0.4×10⁶ cells/0.5 ml for 72 hours at 37° C./5% $CO_2$ in phagocyte culture medium [Advanced DMEM/F12 supplemented with 100 U/ml penicillin/100 μg/ml streptomycin (Thermo-Fisher), 2 mM Glutamax, 55 μM 2-mercaptoethanol, N-2 supplement (Thermo-Fisher), and 100 ng/ml recombinant human M-CSF].

Following co-culture with iPSC-derived phagocytes, tissue sections were fixed in 4% paraformaldehyde and fibrillar plaques were labelled with 0.025% thioflavin S. Fluorescent images were acquired using a slide scanner and analyzed using HALO Image Analysis Software v3.1.1076.423. For measurement of fibrillar plaque area, fluorescent images from control-treated tissue sections were thresholded to highlight dense plaques, and subsequent tissue sections were thresholded with identical parameters. Data are reported as the measured area occupied by dense plaques (thresholded area) expressed as a percentage of total tissue area per section.

Statistical analysis was carried out using Prism Version 8.4.3 (Graph Pad Software). Dense plaque area measurements were analyzed by one-way ANOVA followed by a Dunnett's multiple comparisons test, comparing the means of each AC-264713 treatment group (dose a, dose b, and dose c) to the mean of the control group (0 μg/ml). n=6 tissue sections per group. As shown in FIG. 3, AC-264713 led to statistically significantly reductions in the percent area of amyloid plaques following co-culture with hiPSC-derived phagocytes at dose a, dose b, or dose c (n=6, Adjusted p-value<0.0001 for the comparison of concentrations a to c to 0 μg/ml).

Example 5 In Vivo AC-264713 Exposure and Target Binding (PK/TB) in APPPS1-21 Mice An antibody exposure and target binding in vivo study in APPPS1-21 animals was conducted to determine the brain and serum distribution as well as the in vivo plaque binding potential following AC-264713 administration.

Animals 8.5 to 12.5 months old APPPS1-21 (B6.Cg-Tg(Thy1-APPSw,Thy1-PSEN1*L166P)21Jckr)) (Radde, Bolmont et al. 2006) were used for the PK/TB study. The original breeder mice were obtained by the lab of Mathias Jucker under license agreement with Fa. Koesler (Germany). Mice were bred at Charles River Laboratories (Sulzfeld, Germany) and delivered to the vivarium at AbbVie Deutschland GmbH and aged for the execution of the experiments. Animal health and comfort were veterinary-controlled. Mice were in temperature- and humidity-controlled rooms with a 12:12 hour dark/light cycle with ad libitum access to water and food.

In Vivo Methods

For this study AC-264713 as well as comparator antibody Ab1 were tested in a range of doses 1 to 4, and dosed intravenously via the tail vein. Three female animals were used for each dose. The investigated timepoint was 72 hours p.a. At study termination, blood was drawn at 72 h by cardiac puncture, and serum isolated. The animals were subsequently perfused with cold PBS with 1000 U/L Heparin for 10 min, and the brain dissected, cut in half mid-sagittally, and the right brain hemisphere prepared for immunohistochemistry. The left cortex, the rest of the forebrain and the cerebellum were isolated, flash frozen separately in liquid nitrogen and the left cortex used for quantification of AC-264713 with ELISA.

Tissue Processing, Immunohistochemistry and Analysis of Target Binding

The right hemispheres, employed for immunohistochemistry, were drop-fixed in 10% formalin for 24 hours and then switched to 70% ethanol. Tissue was trimmed and samples dehydrated using a standard ethanol series, followed by xylene and paraffin embedding (ASP300, Leica). Brain hemispheres were randomized based on test article and dose, and paraffin blocks, containing 4 randomized hemispheres, were generated. 4 µm paraffin sections were prepared and processed on an automated stainer, using citrate-buffer-based heat-induced antigen retrieval solution and 3,3'-Diaminobenzidine (DAB)-based detection. For detection of the in vivo-dosed AC-264713 and comparator antibody Ab1, a biotinylated donkey anti-human F(ab')$_2$ fragment detecting human IgG (H+L) (Jackson Immuno) was used at a concentration of at 3.7 µg/mL. The $A\beta_{pE3}$ target area was determined by applying AC-264713 at 0.35 µg/mL or comparator antibody Ab1 at a concentration of 0.26 µg/mL for immunostaining.

Images were collected with a P1000 scanner. To quantify the binding to $A\beta_{pE3}$ for each molecule, the area occupied by AC-264713 or comparator antibody Ab1 was normalized by defining a total target area of $A\beta_{pE3}$ based on AC-264713 or comparator antibody Ab1 IR, respectively, in the plaques from an adjacent section. For that, three matched sections per brain were analyzed using the Area Quantification module in HALO™ image analysis software. For each section, the cortex was outlined. Using the software, the "threshold" was determined by an observer who was blind to the treatment of the animals. The threshold was set so that the positive brown DAB stain of the hIgG or AC-264713 or comparator antibody Ab1 immunoreactivity was recognized by the software and the background/non-specific staining was excluded from the analysis. Once an appropriate threshold was set, the software measured the percentage of the area of interest (cortex) containing the positive immunoreactivity for hIgG or AC-264713 or comparator antibody Ab1. The hIgG IR area in the cortex was then normalized to the AC-264713 IR or Ab1 IR and the values plotted and analyzed in GraphPadPrism (version 8, GraphPad Software). Data was expressed as mean±SEM and analyzed by 1-way ANOVA followed by Kruskal-Wallis multiple comparison test).

Evaluation of AC-264713 Levels in the Serum and the Brain

Serum and brain samples were analyzed for AC-264713 and comparator antibody Ab1 using an electrochemiluminescence immunoassay detecting human IgG1. Briefly, serum was diluted with PBS or PBS containing the appropriate concentration of sample matrix to achieve a final concentration of 1% serum in all samples. The dilution factor was chosen according to expected analyte levels. Samples were measured in three dilutions from which at least two dilutions were in the accepted measurement range. The diluted samples were loaded on a streptavidin plate pre-coated with biotinylated antibody ab99757 (0.5 µg/mL) capturing human IgG1. Plates were incubated for 1 hour, washed with TTBS (Tris Tween Buffered Saline), and human IgG1 was detected with sulfo-tagged EB89 antibody (1 µg/mL)).

For the analysis of brain samples, general assay procedures remained the same. Before the experiment, brain tissue was homogenized 1:5 in homogenization buffer (50 mM Tris (pH 7.5), 150 mM NaCl, 1 mM NaF, 1 mM $Na_2VO_4$, 1 mM EDTA (pH 7.5), 0.25% Na Deoxycholate, 1% NP-40 and 1× protease inhibitor tablet). For the analysis, dilution factors were adjusted appropriately, and were 1:40 for CSF samples, and 1:4 for brain homogenate.

AC-264713 or Ab1 was used for the construction of the respective standard curves and control samples which included the same concentration of biological matrix as the test samples. For the analysis of serum samples, the standard curve was based on seven standard points covering a concentration range from 31 to 7500 ng/mL. For CSF and brain, eleven standard points were used to generate the standard curve covering a concentration range from 0.023 to 1330 ng/mL. The LLOQ for serum was 31 ng/mL, and for brain 0.152 ng/g, respectively for both analytes.

Data Analysis for In Vivo Potency for Target Binding

A nonlinear regression analysis of normalized IR signal as a function of Cortex antibody concentrations was carried out using Prism Version 9.1.0 (Graph Pad Software). A variable slope model, % area covered by immunoreactivity [norm.]=Bottom+X*(Top−Bottom)/(X+EC50), was used, where Top was fixed to 100%.

Image analysis of the hIgG stained sections revealed a dose dependent increase and localization to plaques of the test article AC-264713 and comparator antibody Ab1 in the cortex. Analysis of $A\beta_{pE3}$ immunoreactive plaques and normalization of hIgG IR to Ab1 IR or AC-264713 IR in the cortex also showed a dose dependent increase in plaque coverage of AC-264713 as well as comparator antibody Ab1 (FIG. 4).

All concentrations measured were within the limit of quantification. The concentration increased dose-dependently in both cortex and serum at all doses tested and averaged concentrations of AC-264713 ranged between 0.0016 to 0.29 µg/g in cortex and 4.5 to 352 µg/mL in serum. The tissue to serum ratio (T/S) was between 0.03% and 0.08%.

Correlating observed individual animal brain concentrations and target binding as quantified by IR (FIG. 5), AC-264713 binds to $A\beta_{pE3}$ with an $EC_{50}$ of 0.031 µg/g (confidence interval: 0.016-0.065 µg/g), in comparison to comparator antibody Ab1, which binds with lower potency with an $EC_{50}$ of 0.28 µg/g (confidence interval: 0.13-1.2 µg/g).

Example 6 Evaluation of AC-264713 in an Acute Microhemorrhage Model Using APPPS1-21 Mice An in vivo study was conducted to determine whether an AC-264713 mouse precursor antibody induces microhemorrhages in an acute microhemorrhage model using APPPS1-21 mice.

Animals 15-17 months old APPPS1-21 mice were used in the microhemorrhage study. Mice were breed at Charles River Laboratories (Wilmington, USA) and delivered to the vivarium at the AbbVie Bioresearch Center and aged and transferred to the Cambridge Research Center (CRC) vivarium for the execution of the experiments. Mice were in temperature- and humidity-controlled rooms with a 12:12 hour dark/light cycle with ad libitum access to water and food. Animals in the CRC vivarium were group housed in individually ventilated cages with 12 h:12 h light-dark cycle and ad lib access to food and water. Mice were allowed to acclimate for at least 72 hours before dosing.

In Vivo Methods

The microhemorrhage study was performed in model described previously (Janssens, Hermans et al. 2021) with some modifications. At the age of 15 months, $A\beta_{pE3}$ is detectable in the cerebral vasculature but is not as abundant as some other N-terminal $A\beta$ species in APPPS1-21 mice. Mice (n=4, mixed gender) were given a single dose of AC-233661, or via intraperitoneal injection. A mouse IgG was used as negative control (n=4, mixed gender) and a comparator antibody Ab2 with mu IgG2a/k that caused ARIA in patients with AD was used as positive control (n=5). Both the negative and positive control were administered via intraperitoneal injection. Three days after injection, or as soon as severe adverse effects were observed (whichever came first), mice were euthanized with sodium pentobarbital, perfused with PBS, and the brains were quickly removed.

Histology Analysis for Microhemorrhage

The right hemispheres of the brain were then drop-fixed in 10% formalin for 24 hours and then switched to PBS containing 30% sucrose. Serial coronal sections at 50 m thickness were collected from the rostral to the caudal end of each brain hemisphere using a freezing sliding microtome.

For red blood cell quantification, every $12^{th}$ section was mounted on glass slides, counterstained with hematoxylin.

The hemosiderin deposits were stained via Prussian Blue staining. Every $12^{th}$ section was mounted on glass slides. Then the sections were rehydrated in PBS and permeabilized in PBS containing 0.25% Triton-X-100. After incubation in 80% ethanol containing saturated NaCl and 0.01M NaOH, the sections were incubated in 80% ethanol containing saturated NaCl, 0.01M NaOH and 0.5% Congo Red. Then the slides were washed in 80% ethanol and normal saline followed by incubation in 2% potassium ferrocyanide in 0.12 M HCl. After washing in PBS, the slides were dehydrated, cover-slipped and scanned.

Once scanned using a slide scanner, the brain sections were analyzed using the Area Quantification module in HALO™ image analysis software. Using the software, the entire sections were outlined, and the "threshold" was determined by an observer who was blind to the treatment of the animals. The threshold was set so that the red blood cells or the Prussian Blue signal was recognized by the software and the background/non-specific staining was excluded from the analysis. Once an appropriate threshold was set, the software measured the percentage of the area of interest (entire section) containing the positive signal. For each animal, the mean value from the set of serial sections with a 600 μm interval was calculated.

The comparator antibody Ab2 induced significant microhemorrhage within three days. In contrast, the mouse precursor antibody of AC-264713 treated APPPS1-21 mice remained healthy during this period, and the red blood cell and hemosiderin deposits were comparable to the negative control mIgG2a/k antibody (FIG. 6).

Summary of Examples

AC-264713 binds to human $A\beta_{pE3-42}$ fibrils with an $EC_{50}$ of 0.7 nM in direct binding ELISA. AC-264713 did not cross-react with another human pyroglutamate-modified $A\beta$ species, $A\beta_{pE11-40}$. AC-264713 also did not cross-react with A01-40 from all species including human, monkey, dog, rabbit, rat, and mouse. Additionally, amino acid residues pyro, 3, 4 and 5 may be critical for AC-264713 binding to $Ab_{pE3-42}$. The immunostaining on unfixed brain tissue demonstrated that AC-264713 binds to AD brains that contains amyloid plaques in a dose-dependent manner with an $EC_{50}$ of 0.4 μg/ml, while it does not bind to non-AD human, rat or cynomolgus monkey brain tissue where the amyloid plaques do not present. When AC-264713 was tested in an ex vivo phagocytosis assay at concentrations a to c, it activated hiPSC-derived phagocytes to remove plaques. Three days after AC-264713 was systemically injected into APPPS1-21 mice after a single IV injection, it was detected in brain and serum with dose-dependent increase in exposure, and bound the plaques in a dose-dependent manner. In an acute microhemorrhage model using APPPS1-21 mice, AC-264713 mouse precursor antibody did not cause microhemorrhage within 3 days after a single IP injection. Taken together, the in vitro and in vivo data illustrate the proposed mode of action of AC-264713, i.e., an anti $A\beta_{pE3}$ monoclonal antibody with full effector function that can bind the amyloid plaques in the brain after peripheral administration and activate microglial phagocytosis. The foregoing indicates the suitability of AC-264713 for use to treat Alzheimer's disease by removing the amyloid plaques from an AD brain.

9. EXEMPLARY EMBODIMENTS

While various specific embodiments have been illustrated and described, some are represented below. It will be appreciated that various changes can be made without departing from the spirit and scope of the inventive concept(s).

1. An anti-human $A\beta_{pE3}$ antibody which comprises (i) a variable heavy chain (vH) including 3 CDRs; and (ii) a variable light chain (vL) including 3 CDRs, wherein:

```
                                    (SEQ ID NO: 1)
    vH CDR1 is GFSLSTSGMGVS;

(SEQ ID NO: 2)
    vH CDR2 is HIYWDDDKRYNPYMKR;

(SEQ ID NO: 3)
    vH CDR3 is RADDYDVGFAY;

(SEQ ID NO: 4)
    vL CDR1 is LASQTIGTWLA;
```

-continued

```
                                       (SEQ ID NO: 5)
vL CDR2 is AATSLAD;
and
                                       (SEQ ID NO: 6)
vL CDR3 is QQLYSSPFT.
```

2. The anti-human Aβ$_{pE3}$ antibody of embodiment 1, wherein the antibody comprises a heavy chain variable region including the amino acid sequence set forth as SEQ ID NO:7 and a light chain variable region including the amino acid sequence set forth as SEQ ID NO:8.

3. The anti-human Aβ$_{pE3}$ antibody of embodiment 1, wherein the antibody comprises a heavy chain including the amino acid sequence set forth as SEQ ID NO:9 and a light chain including the amino acid sequence set forth as SEQ ID NO:10.

4. The anti-human Aβ$_{pE3}$ antibody of embodiment 1, wherein the antibody comprises an IgG constant region.

5. The anti-human Aβ$_{pE3}$ antibody of embodiment 4, wherein the antibody comprises a human heavy chain constant region including an Fc portion, wherein the Fc portion is a human IgG1, IgG2, IgG3, IgG4, or IgM isotype.

6. The anti-human Aβ$_{pE3}$ antibody of embodiment 5, wherein the antibody comprises a kappa light chain constant region.

7. A composition including the anti-human Aβ$_{pE3}$ antibody of embodiment 1.

8. A method for treating a neurodegenerative disorder including administering the anti-human Aβ$_{pE3}$ antibody of embodiment 1 to a patient in need thereof.

9. The method of embodiment 8, wherein the neurodegenerative disorder is Alzheimer's disease (AD).

10. A polynucleotide including a nucleotide sequence encoding an anti-human Aβ$_{pE3}$ antibody, wherein the antibody comprises (i) a vH chain including three CDRs; and (ii) a vL chain including three CDRs, wherein:

```
                                       (SEQ ID NO: 1)
vH CDR1 is GFSLSTSGMGVS;

(SEQ ID NO: 2)
vH CDR2 is HIYWDDDKRYNPYMKR;

(SEQ ID NO: 3)
vH CDR3 is RADDYDVGFAY;

(SEQ ID NO: 4)
vL CDR1 is LASQTIGTWLA;

(SEQ ID NO: 5)
vL CDR2 is AATSLAD;
and
                                       (SEQ ID NO: 6)
vL CDR3 is QQLYSSPFT.
```

11. A vector including the polynucleotide of embodiment 10.

12. A eukaryotic host cell transformed with the vector of embodiment 11.

13. The eukaryotic host cell of embodiment 12, which is a mammalian host cell.

14. A method for producing an anti-human Aβ$_{pE3}$ antibody including: (a) culturing the eukaryotic host cell of embodiment 13 and (b) recovering the anti-human Aβ$_{pE3}$ antibody.

15. An anti-human Aβ$_{pE3}$ antibody, wherein the antibody comprises two heavy chains, each heavy chain comprising the amino acid sequence set forth as SEQ ID NO: 37 and two light chains, each light chain comprising the amino acid sequence set forth as SEQ ID NO: 10.

One skilled in the art will readily appreciate that the present inventive concept is well adapted to carry out the objects and obtain the ends and advantages mentioned, as well as those inherent therein. The particular embodiments described herein are intended to be representative and exemplary and are not intended as limitations on the scope of the invention. Changes therein and other uses will be apparent to those skilled in the art which are encompassed within the spirit of the invention as defined by the scope of the claims.

REFERENCES

Aisen, P. S., J. Cummings, R. Doody, L. Kramer, S. Salloway, D. J. Selkoe, J. Sims, R. A. Sperling and B. Vellas (2020). "The Future of Anti-Amyloid Trials." *J Prev Alzheimers Dis* 7(3): 146-151.

Greenberg, S. M., B. J. Bacskai, M. Hernandez-Guillamon, J. Pruzin, R. Sperling and S. J. van Veluw (2020). "Cerebral amyloid angiopathy and Alzheimer disease—one peptide, two pathways." *Nat Rev Neurol* 16(1): 30-42.

Haenseler, W., S. N. Sansom, J. Buchrieser, S. E. Newey, C. S. Moore, F. J. Nicholls, S. Chintawar, C. Schnell, J. P. Antel, N. D. Allen, M. Z. Cader, R. Wade-Martins, W. S. James and S. A. Cowley (2017). "A Highly Efficient Human Pluripotent Stem Cell Microglia Model Displays a Neuronal-Co-culture-Specific Expression Profile and Inflammatory Response." *Stem Cell Reports* 8(6): 1727-1742.

Janssens, J., B. Hermans, M. Vandermeeren, E. Barale-Thomas, M. Borgers, R. Willems, G. Meulders, C. Wintmolders, D. Van den Bulck, A. Bottelbergs, L. Ver Donck, P. Larsen, D. Moechars, W. Edwards, M. Mercken and B. Van Broeck (2021). "Passive immunotherapy with a novel antibody against 3pE-modified Abeta demonstrates potential for enhanced efficacy and favorable safety in combination with BACE inhibitor treatment in plaque-depositing mice." *Neurobiol Dis* 154: 105365.

Jawhar, S., O. Wirths and T. A. Bayer (2011). "Pyroglutamate amyloid-beta (Abeta): a hatchet man in Alzheimer disease." *J Biol Chem* 286(45): 38825-38832.

Kuo, Y. M., M. R. Emmerling, A. S. Woods, R. J. Cotter and A. E. Roher (1997). "Isolation, chemical characterization, and quantitation of A beta 3-pyroglutamyl peptide from neuritic plaques and vascular amyloid deposits." *Biochem Biophys Res Commun* 237(1): 188-191.

Penninkilampi, R., H. M. Brothers and G. D. Eslick (2017). "Safety and Efficacy of Anti-Amyloid-β Immunotherapy in Alzheimer's Disease: A Systematic Review and Meta-Analysis." *J Neuroimmune Pharmacol* 12(1): 194-203.

Radde, R., T. Bolmont, S. A. Kaeser, J. Coomaraswamy, D. Lindau, L. Stoltze, M. E. Calhoun, F. Jaggi, H. Wolburg, S. Gengler, C. Haass, B. Ghetti, C. Czech, C. Holscher, P. M. Mathews and M. Jucker (2006). "Abeta42-driven cerebral amyloidosis in transgenic mice reveals early and robust pathology." *EMBO Rep* 7(9): 940-946.

Selkoe, D. J. and J. Hardy (2016). "The amyloid hypothesis of Alzheimer's disease at 25 years." *EMBO Mol Med* 8(6): 595-608.

Sperling, R. A., C. R. Jack, Jr., S. E. Black, M. P. Frosch, S. M. Greenberg, B. T. Hyman, P. Scheltens, M. C. Carrillo, W. Thies, M. M. Bednar, R. S. Black, H. R. Brashear, M.

Grundman, E. R. Siemers, H. H. Feldman and R. J. Schindler (2011). "Amyloid-related imaging abnormalities in amyloid-modifying therapeutic trials: recommendations from the Alzheimer's Association Research Roundtable Workgroup." *Alzheimers Dement* 7(4): 367-385.

van Dyck, C. H. (2018). "Anti-Amyloid-beta Monoclonal Antibodies for Alzheimer's Disease: Pitfalls and Promise." *Biol Psychiatry* 83(4): 311-319.

van Dyck, C. H. (2018). "Anti-amyloid-β monoclonal antibodies for Alzheimer's disease: pitfalls and promise." *Biol Psychiatry* 83(4): 311-319.

van Wilgenburg, B., C. Browne, J. Vowles and S. A. Cowley (2013). "Efficient, long-term production of monocyte-derived macrophages from human pluripotent stem cells under partly-defined and fully-defined conditions." PLoS One 8(8): e71098.

What is claimed:

1. An anti-human Aβ$_{pE3}$ antibody which comprises (i) a variable heavy chain (vH) comprising 3 CDRs; and (ii) a variable light chain (vL) comprising 3 CDRs, wherein:

vH CDR1 is GFSLSTSGMGVS; (SEQ ID NO: 1)

vH CDR2 is HIYWDDDKRYNPYMKR; (SEQ ID NO: 2)

vH CDR3 is RADDYDVGFAY; (SEQ ID NO: 3)

vL CDR1 is LASQTIGTWLA; (SEQ ID NO: 4)

-continued

```
                              (SEQ ID NO: 5)
vL CDR2 is AATSLAD;
and (SEQ ID NO: 6)
vL CDR3 is QQLYSSPFT.
```

2. The anti-human $Aβ_{pE3}$ antibody of claim 1, wherein the antibody comprises a heavy chain variable region comprising the amino acid sequence set forth as SEQ ID NO:7 and a light chain variable region comprising the amino acid sequence set forth as SEQ ID NO:8.

3. An anti-human $Aβ_{pE3}$ antibody which comprises two heavy chains, each heavy chain comprising the amino acid sequence set forth as SEQ ID NO:9, and two light chains, each light chain comprising the amino acid sequence set forth as SEQ ID NO:10.

4. An anti-human $Aβ_{pE3}$ antibody, wherein the antibody comprises two heavy chains, each heavy chain comprising the amino acid sequence set forth as SEQ ID NO: 37 and two light chains, each light chain comprising the amino acid sequence set forth as SEQ ID NO: 10.

5. The anti-human $Aβ_{pE3}$ antibody of claim 1, wherein the antibody comprises a human IgG1 constant region.

6. The anti-human $Aβ_{pE3}$ antibody of claim 5, wherein the antibody comprises a kappa light chain constant region.

* * * * *

SEQUENCE LISTING

```
Sequence total quantity: 37
SEQ ID NO: 1            moltype = AA  length = 12
FEATURE                 Location/Qualifiers
REGION                  1..12
                        note = AC-264713 vH CDR1 sequence
source                  1..12
                        mol_type = protein
                        organism = synthetic construct
SEQUENCE: 1
GFSLSTSGMG VS                                                        12

SEQ ID NO: 2            moltype = AA  length = 16
FEATURE                 Location/Qualifiers
REGION                  1..16
                        note = AC-264713 vH CDR2 sequence
source                  1..16
                        mol_type = protein
                        organism = synthetic construct
SEQUENCE: 2
HIYWDDDKRY NPYMKR                                                    16

SEQ ID NO: 3            moltype = AA  length = 11
FEATURE                 Location/Qualifiers
REGION                  1..11
                        note = AC-264713 vH CDR3 sequence
source                  1..11
                        mol_type = protein
                        organism = synthetic construct
SEQUENCE: 3
RADDYDVGFA Y                                                         11

SEQ ID NO: 4            moltype = AA  length = 11
FEATURE                 Location/Qualifiers
REGION                  1..11
                        note = AC-264713 vL CDR1 sequence
source                  1..11
                        mol_type = protein
                        organism = synthetic construct
SEQUENCE: 4
LASQTIGTWL A                                                         11

SEQ ID NO: 5            moltype = AA  length = 7
FEATURE                 Location/Qualifiers
REGION                  1..7
                        note = AC-264713 vL CDR2 sequence
source                  1..7
                        mol_type = protein
                        organism = synthetic construct
SEQUENCE: 5
AATSLAD                                                              7

SEQ ID NO: 6            moltype = AA  length = 9
FEATURE                 Location/Qualifiers
REGION                  1..9
                        note = AC-264713 vL CDR3 sequence
source                  1..9
                        mol_type = protein
                        organism = synthetic construct
SEQUENCE: 6
QQLYSSPFT                                                            9
```

```
SEQ ID NO: 7              moltype = AA  length = 121
FEATURE                   Location/Qualifiers
REGION                    1..121
                          note = AC-264713 vH region sequence
source                    1..121
                          mol_type = protein
                          organism = synthetic construct
SEQUENCE: 7
EVQLQESGPG LVKPSQTLSL TCTFSGFSLS TSGMGVSWIR QPPGKGLEWL AHIYWDDDKR   60
YNPYMKRRLT ISKDTSKNQV SLKISSVTAA DTAVYYCARR ADDYDVGFAY WGQGTLVTVS  120
S                                                                 121

SEQ ID NO: 8              moltype = AA  length = 107
FEATURE                   Location/Qualifiers
REGION                    1..107
                          note = AC-264713 vL region sequence
source                    1..107
                          mol_type = protein
                          organism = synthetic construct
SEQUENCE: 8
DIQMTQSPSS VSASVGDRVT ITCLASQTIG TWLAWYQQKP GKSPKLLIYA ATSLADGVPS   60
RFSGSGSGTD FTLTISSLQP EDFATYYCQQ LYSSPFTFGQ GTKLEIK                107

SEQ ID NO: 9              moltype = AA  length = 451
FEATURE                   Location/Qualifiers
REGION                    1..451
                          note = AC-264713 heavy chain sequence
source                    1..451
                          mol_type = protein
                          organism = synthetic construct
SEQUENCE: 9
EVQLQESGPG LVKPSQTLSL TCTFSGFSLS TSGMGVSWIR QPPGKGLEWL AHIYWDDDKR   60
YNPYMKRRLT ISKDTSKNQV SLKISSVTAA DTAVYYCARR ADDYDVGFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 10             moltype = AA  length = 214
FEATURE                   Location/Qualifiers
REGION                    1..214
                          note = AC-264713 light chain sequence
source                    1..214
                          mol_type = protein
                          organism = synthetic construct
SEQUENCE: 10
DIQMTQSPSS VSASVGDRVT ITCLASQTIG TWLAWYQQKP GKSPKLLIYA ATSLADGVPS   60
RFSGSGSGTD FTLTISSLQP EDFATYYCQQ LYSSPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 11             moltype = AA  length = 451
FEATURE                   Location/Qualifiers
REGION                    1..451
                          note = AC-233661 heavy chain sequence
source                    1..451
                          mol_type = protein
                          organism = synthetic construct
SEQUENCE: 11
QVTLKESGPG ILQPSQTLSL TCSFSGFSLS TSGMGVSWIR QPSGKGLEWL AHIYWDDDKR   60
YNPYMKRRLT ISKDTSSNQV LLKITSVDTA DTATYYCARR ADDYDVGFAY WGQGTLVTVS  120
SAKTTAPSVY PLAPVCGDTT GSSVTLGCLV KGYFPEPVTL TWNSGSLSSG VHTFPAVLQS  180
DLYTLSSSVT VTSSTWPSQS ITCNVAHPAS STKVDKKIEP RGPTIKPCPP CKCPAPNLLG  240
GPSVFIFPPK IKDVLMISLS PIVTCVVVDV SEDDPDVQIS WFVNNVEVHT AQTQTHREDY  300
NSTLRVVSAL PIQHQDWMSG KEFKCKVNNK DLPAPIERTI SKPKGSVRAP QVYVLPPPEE  360
EMTKKQVTLT CMVTDFMPED IYVEWTNNGK TELNYKNTEP VLDSDGSYFM YSKLRVEKKN  420
WVERNSYSCS VVHEGLHNHH TTKSFSRTPG K                                451

SEQ ID NO: 12             moltype = AA  length = 214
FEATURE                   Location/Qualifiers
REGION                    1..214
                          note = AC-233661 light chain sequence
source                    1..214
                          mol_type = protein
                          organism = synthetic construct
```

SEQUENCE: 12
```
DIVMTQSPAS QSASLGESVT ITCLASQTIG TWLAWYQQKP GKSPQLLIYA ATSLADGVPS  60
RFSGSGSGTK FSFKISSLQA EDFVSYYCQQ LYSSPFTFGS GTKLEIKRAD AAPTVSIFPP 120
SSEQLTSGGA SVVCFLNNFY PKDINVKWKI DGSERQNGVL NSWTDQDSKD STYSMSSTLT 180
LTKDEYERHN SYTCEATHKT STSPIVKSFN RNEC                            214
```

| | |
|---|---|
| SEQ ID NO: 13 | moltype = DNA  length = 1353 |
| FEATURE | Location/Qualifiers |
| misc_feature | 1..1353 |
| | note = AC-264713 heavy chain coding sequence |
| source | 1..1353 |
| | mol_type = other DNA |
| | organism = synthetic construct |

SEQUENCE: 13
```
gaagtgcagc tgcaagagtc cggcccgggc ttggtcaagc cgtcgcagac cctcagcctt   60
acttgcacct tctcgggatt ctcgctgtcc actagcggca tgggcgtgtc gtggatcagg  120
cagcctcctg gcaaagggct ggagtggctt gcccacatct actgggacga tgacaagaga  180
tacaacccct atatgaagcg ccgcctgacc atcagcaagg acacctccaa aaaccaagtc  240
tcgctgaaga tctcctccgt gaccgccgcg gataccgccg tgtactactg cgcccggcgg  300
gccgacgact atgacgtggg atttgcgtac tggggacagg ggaccctggt caccgtgtcc  360
tccgcctcaa ctaagggacc cagcgtgttc cctctcgccc catcatcgaa gtccactagt  420
ggcgggaccg ctgctctcgg ttgtctggtt aaggactact cccggaacc cgtcaccgta  480
tcatggaact ccggtgcact gacatccggc gtgcacacct tcccggccgt gctgcaaagc  540
tccgactgt actccctgtc gagcgtggtc actgtgccct catcaagcct gggtactcag  600
acgtacattt gcaacgtgaa ccacaagccg tccaacacca aggtcgacaa gaaagtggag  660
ccgaagtcct gcgacaagac ccatacttgc ccgccgtgcc cagccctga gctgctgggt  720
ggaccgagcg tgttcctgtt cccacctaaa cccaaggaca ccctgatgat tagccgcacc  780
cccgaagtga cctgtgtggt cgtggatgtg tcccacgaag atcccgaagt caagttcaat  840
tggtacgtgg acggcgtcga agtgcataac gccaagacta gccccgcga ggaacagtac  900
aacagcacct accgggtggt gtccgtgctc actgtcctgc accaagactg gctgaacgga  960
aaggagtaca agtgcaaagt gtccaacaag gcactgccag cgcccatcga gaaaaccatc 1020
agcaaggcca agggccagcc gagagaacct caggtctaca ccctgccgcc atcccgggaa 1080
gaaatgacca gaaccaagt gtcccttacc tgtctcgtga agggattcta cccttccgac 1140
atcgccgtgg agtgggagtc caatggacag ccggagaaca actaccctcct 1200
gtgctggact ccgatggatc tttcttcctg tactcgaagc tcaccgtgga taagcgcgg 1260
tggcaacagg ggaatgtgtt cagctgctcc gtgatgcacg aagctctgca taaccactac 1320
actcagaagt cgctgtcact ctccccggg aaa                             1353
```

| | |
|---|---|
| SEQ ID NO: 14 | moltype = DNA  length = 642 |
| FEATURE | Location/Qualifiers |
| misc_feature | 1..642 |
| | note = AC-264713 light chain coding sequence |
| source | 1..642 |
| | mol_type = other DNA |
| | organism = synthetic construct |

SEQUENCE: 14
```
gacatccaga tgacccagtc cccgtcctcg gtgtcagcgt cagtggggga cagggtcacg   60
atcacttgcc tggccagcca gaccattggc acttggctgg cctggtatca gcagaagccc  120
ggaaagtcac cgaagctgtt gatctacgcc gcaacttccc tggccgatgg cgtgccctcg  180
cggttctccg gttccgggtc gggaactgac tttaccctga ccattagctc tctgcaacct  240
gaggacttcg ccacctacta ctgtcagcaa ctgtactcct cgccgttcac cttcggacaa  300
ggcaccaagt tggaaataaa gcggactgtg gcggcaccca gcgtgttcat cttttctcca  360
tccgacgaac agctgaagtc cggtaccgct agcgtggtct gtctcctgaa caacttctac  420
ccgcgcgagg ccaaggtcca gtggaaggtc gacaacgcgc tccagagcgg caacagtcag  480
gaatccgtga ccgaacagga ctccaaggat tcgacctact cgctgtcctc cactctcacc  540
ctgtccaaag ccgattacga gaagcacaaa gtgtacgctt gcgaagtgac ccatcaaggc  600
cttagcagcc ccgtgacaaa gtccttcaat cgggagagt gc                     642
```

| | |
|---|---|
| SEQ ID NO: 15 | moltype = DNA  length = 1353 |
| FEATURE | Location/Qualifiers |
| misc_feature | 1..1353 |
| | note = AC-233661 heavy chain coding sequence |
| source | 1..1353 |
| | mol_type = other DNA |
| | organism = synthetic construct |

SEQUENCE: 15
```
caggttactc tgaaagagtc tggccctggg atattgcagc cctcccagac cctcagtctg   60
acttgttctt tctctgggtt ttcactgagc acttctggta tgggtgtgag ctggattcgt  120
cagccctcag gaaagggtct ggagtggctg gcacacattt actgggatga tgacaagcgt  180
tataacccat acatgaagag acggctcaca atctccaagg atacctccag caaccaggta  240
ctcctcaaga tcaccagtgt ggacactgca gatactgcca catactactg tgctcgaaga  300
gctgacgatt acgacgtggg gtttgcttac tggggccaag ggactctggt caccgtctcc  360
tcagctaaaa caacagcccc atcggtctat ccactggccc ctgtgtgtgg agatacaact  420
ggctcctcgg tgactctagg atgcctggtc aagggttatt tccctgagcc agtgaccttg  480
acctggaact ctggatccct gtccagtggt gtgcacacct tcccagctgt cctgcagtct  540
gacctctaca ccctcagcag ctcagtgact gtaacctcga gcacctggcc cagcagtcc  600
atcacctgca atgtggccca cccggcaagc agcaccaagg tggacaagaa aattgagccc  660
agagggccca caatcaagcc ctgtcctcca tgcaaatgcc cagcacctaa cctcttgggt  720
ggaccatccg tcttcatctt ccctccaaag atcaaggatg tactcatgat ctccctgagc  780
```

-continued

```
cccatagtca catgtgtggt ggtggatgtg agcgaggatg acccagatgt ccagatcagc   840
tggtttgtga acaacgtgga agtacacaca gctcagacac aaacccatag agaggattac   900
aacagtactc tccgggtggt cagtgccctc cccatccagc accaggactg gatgagtggc   960
aaggagttca aatgcaaggt caacaacaaa gacctcccag cgcccatcga gagaaccatc  1020
tcaaaaccca aagggtcagt aagagctcca caggtatatg tcttgcctcc accagaagaa  1080
gagatgacta agaaacaggt cactctgacc tgcatggtca cagacttcat gcctgaagac  1140
atttacgtgg agtggaccaa caacgggaaa acagagctaa actacaagaa cactgaacca  1200
gtcctggact ctgatggttc ttacttcatg tacagcaagc tgagagtgga aaagaagaac  1260
tgggtggaaa gaaatagcta ctcctgttca gtggtccacg agggtctgca caatcaccac  1320
acgactaaga gcttctcccg gactccgggt aaa                                1353

SEQ ID NO: 16          moltype = DNA   length = 642
FEATURE                Location/Qualifiers
misc_feature           1..642
                       note = AC-233661 light chain coding sequence
source                 1..642
                       mol_type = other DNA
                       organism = synthetic construct
SEQUENCE: 16
gatattgtga tgacccagtc tcctgcctcc cagtctgcat ctctgggaga aagtgtcacc    60
atcacatgcc tggcaagtca gaccattggt acatggttag catggtatca gcagaaacca   120
gggaaatctc ctcagctcct gatttatgct gcaaccaatt tggcagatgg ggtcccatca   180
aggttcagtg gtagtggatc tggcacaaaa ttttctttca agatcagcag cctacaggtg   240
gaagattttg taagttatta ctgtcaacaa ctttacagta gtccattcac gttcggctcg   300
gggacaaagt tggaaataaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gt                      642

SEQ ID NO: 17          moltype = AA   length = 40
FEATURE                Location/Qualifiers
SITE                   1
                       note = MISC_FEATURE - X is pyroglutamic acid
source                 1..40
                       mol_type = protein
                       organism = Homo sapiens
SEQUENCE: 17
XFRHDSGYEV HHQKLVFFAE DVGSNKGAII GLMVGGVVIA                           40

SEQ ID NO: 18          moltype = AA   length = 30
FEATURE                Location/Qualifiers
SITE                   1
                       note = MISC_FEATURE - X is pyroglutamic acid
source                 1..30
                       mol_type = protein
                       organism = Homo sapiens
SEQUENCE: 18
XVHHQKLVFF AEDVGSNKGA IIGLMVGGVV                                      30

SEQ ID NO: 19          moltype = AA   length = 40
FEATURE                Location/Qualifiers
source                 1..40
                       mol_type = protein
                       organism = Homo sapiens
SEQUENCE: 19
EFRHDSGYEV HHQKLVFFAE DVGSNKGAII GLMVGGVVIA                           40

SEQ ID NO: 20          moltype = AA   length = 40
FEATURE                Location/Qualifiers
source                 1..40
                       mol_type = protein
                       organism = Homo sapiens
SEQUENCE: 20
DAEFRHDSGY EVHHQKLVFF AEDVGSNKGA IIGLMVGGVV                           40

SEQ ID NO: 21          moltype = AA   length = 42
FEATURE                Location/Qualifiers
source                 1..42
                       mol_type = protein
                       organism = Homo sapiens
SEQUENCE: 21
DAEFRHDSGY EVHHQKLVFF AEDVGSNKGA IIGLMVGGVV IA                        42
```

```
SEQ ID NO: 22           moltype = AA  length = 40
FEATURE                 Location/Qualifiers
source                  1..40
                        mol_type = protein
                        organism = Mus musculus
SEQUENCE: 22
DAEFGHDSGF EVRHQKLVFF AEDVGSNKGA IIGLMVGGVV                              40

SEQ ID NO: 23           moltype = AA  length = 445
FEATURE                 Location/Qualifiers
REGION                  1..445
                        note = PR-1918940 heavy chain sequence
source                  1..445
                        mol_type = protein
                        organism = synthetic construct
SEQUENCE: 23
QVQLVQSGAE VKKPGSSVKV SCKASGYDFT RYYINWVRQA PGQGLEWMGW INPGSGNTKY        60
NEKFKGRVTI TADESTSTAY MELSSLRSED TAVYYCAREG ITVYWGQGTT VTVSSASTKG       120
PSVFPLAPSS KSTSGGTAAL GCLVKDYFPE PVTVSWNSGA LTSGVHTFPA VLQSSGLYSL       180
SSVVTVPSSS LGTQTYICNV NHKPSNTKVD KKVEPKSCDK THTCPPCPAP ELLGGPSVFL       240
FPPKPKDTLM ISRTPEVTCV VVDVSHEDPE VKFNWYVDGV EVHNAKTKPR EEQYNSTYRV       300
VSVLTVLHQD WLNGKEYKCK VSNKALPAPI EKTISKAKGQ PREPQVYTLP PSREEMTKNQ       360
VSLTCLVKGF YPSDIAVEWE SNGQPENNYK TTPPVLDSDG SFFLYSKLTV DKSRWQQGNV       420
FSCSVMHEAL HNHYTQKSLS LSPGK                                            445

SEQ ID NO: 24           moltype = AA  length = 219
FEATURE                 Location/Qualifiers
REGION                  1..219
                        note = PR-1918940 light chain sequence
source                  1..219
                        mol_type = protein
                        organism = synthetic construct
SEQUENCE: 24
DIVMTQTPLS LSVTPGQPAS ISCKSSQSLL YSRGKTYLNW LLQKPGQSPQ LLIYAVSKLD        60
SGVPDRFSGS GSGTDFTLKI SRVEAEDVGV YYCVQGTHYP FTFGQGTKLE IKRTVAAPSV       120
FIFPPSDEQL KSGTASVVCL LNNFYPREAK VQWKVDNALQ SGNSQESVTE QDSKDSTYSL       180
SSTLTLSKAD YEKHKVYACE VTHQGLSSPV TKSFNRGEC                             219

SEQ ID NO: 25           moltype = AA  length = 449
FEATURE                 Location/Qualifiers
REGION                  1..449
                        note = PR-1770097 heavy chain sequence
source                  1..449
                        mol_type = protein
                        organism = synthetic construct
SEQUENCE: 25
EVQLLESGGG LVQPGGSLRL SCAASGFTFS NYGMSWVRQA PGKGLEWVAS IRSGGGRTYY        60
SDNVKGRFTI SRDNSKNTLY LQMNSLRAED TAVYYCVRYD HYSGSSDYWG QGTLVTVSSA       120
KTTAPSVYPL APVCGDTTGS SVTLGCLVKG YFPEPVTLTW NSGSLSSGVH TFPAVLQSDL       180
YTLSSSVTVT SSTWPSQSIT CNVAHPASST KVDKKIEPRG PTIKPCPPCK CPAPNLLGGP       240
SVFIFPPKIK DVLMISLSPI VTCVVVDVSE DDPDVQISWF VNNVEVHTAQ TQTHREDYNS       300
TLRVVSALPI QHQDWMSGKE FKCKVNNKDL PAPIERTISK PKGSVRAPQV YVLPPPEEEM       360
TKKQVTLTCM VTDFMPEDIY VEWTNNGKTE LNYKNTEPVL DSDGSYFMYS KLRVEKKNWV       420
ERNSYSCSVV HEGLHNHHTT KSFSRTPGK                                        449

SEQ ID NO: 26           moltype = AA  length = 219
FEATURE                 Location/Qualifiers
REGION                  1..219
                        note = PR-1770097 light chain sequence
source                  1..219
                        mol_type = protein
                        organism = synthetic construct
SEQUENCE: 26
DVVMTQSPLS LPVTPGEPAS ISCKSSQSLL DSDGKTYLNW LLQKPGQSPQ RLIYLVSKLD        60
SGVPDRFSGS GSGTDFTLKI SRVEAEDVGV YYCWQGTHFP RTFGQGTKVE IKRADAAPTV       120
SIFPPSSEQL TSGGASVVCF LNNFYPKDIN VKWKIDGSER QNGVLNSWTD QDSKDSTYSM       180
SSTLTLTKDE YERHNSYTCE ATHKTSTSPI VKSFNRNEC                             219

SEQ ID NO: 27           moltype = AA  length = 14
FEATURE                 Location/Qualifiers
REGION                  1..14
                        note = Anti-amyloid beta epitope identifying peptide
SITE                    1
                        note = MISC_FEATURE - X is pyroglutamic acid
SITE                    14
                        note = MISC_FEATURE - Biotinylation
```

```
source                    1..14
                          mol_type = protein
                          organism = synthetic construct
SEQUENCE: 27
XFRHDSGYEV HHQK                                                         14

SEQ ID NO: 28             moltype = AA   length = 13
FEATURE                   Location/Qualifiers
REGION                    1..13
                          note = Anti-amyloid beta epitope identifying peptide
SITE                      13
                          note = MISC_FEATURE - Biotinylation
source                    1..13
                          mol_type = protein
                          organism = synthetic construct
SEQUENCE: 28
FRHDSGYEVH HQK                                                          13

SEQ ID NO: 29             moltype = AA   length = 12
FEATURE                   Location/Qualifiers
REGION                    1..12
                          note = Anti-amyloid beta epitope identifying peptide
SITE                      12
                          note = MISC_FEATURE - Biotinylation
source                    1..12
                          mol_type = protein
                          organism = synthetic construct
SEQUENCE: 29
RHDSGYEVHH QK                                                           12

SEQ ID NO: 30             moltype = AA   length = 14
FEATURE                   Location/Qualifiers
REGION                    1..14
                          note = Anti-amyloid beta epitope identifying peptide
SITE                      14
                          note = MISC_FEATURE - Biotinylation
source                    1..14
                          mol_type = protein
                          organism = synthetic construct
SEQUENCE: 30
EFRHDSGYEV HHQK                                                         14

SEQ ID NO: 31             moltype = AA   length = 14
FEATURE                   Location/Qualifiers
REGION                    1..14
                          note = Anti-amyloid beta epitope identifying peptide
SITE                      1
                          note = MISC_FEATURE - X is pyroglutamic acid
SITE                      14
                          note = MISC_FEATURE - Biotinylation
source                    1..14
                          mol_type = protein
                          organism = synthetic construct
SEQUENCE: 31
XGRHDSGYEV HHQK                                                         14

SEQ ID NO: 32             moltype = AA   length = 14
FEATURE                   Location/Qualifiers
REGION                    1..14
                          note = Anti-amyloid beta epitope identifying peptide
SITE                      1
                          note = MISC_FEATURE - X is pyroglutamic acid
SITE                      14
                          note = MISC_FEATURE - Biotinylation
source                    1..14
                          mol_type = protein
                          organism = synthetic construct
SEQUENCE: 32
XFGHDSGFEV HHQK                                                         14

SEQ ID NO: 33             moltype = AA   length = 14
FEATURE                   Location/Qualifiers
REGION                    1..14
                          note = Anti-amyloid beta epitope identifying peptide
SITE                      1
                          note = MISC_FEATURE - X is pyroglutamic acid
SITE                      14
                          note = MISC_FEATURE - Biotinylation
```

```
SEQ ID NO: 33 (continued)
source                  1..14
                        mol_type = protein
                        organism = synthetic construct
SEQUENCE: 33
XFRGDSGYEV HHQK                                                         14

SEQ ID NO: 34           moltype = AA  length = 14
FEATURE                 Location/Qualifiers
REGION                  1..14
                        note = Anti-amyloid beta epitope identifying peptide
SITE                    1
                        note = MISC_FEATURE - X is pyroglutamic acid
SITE                    14
                        note = MISC_FEATURE - Biotinylation
source                  1..14
                        mol_type = protein
                        organism = synthetic construct
SEQUENCE: 34
XFRHGSGYEV HHQK                                                         14

SEQ ID NO: 35           moltype = AA  length = 14
FEATURE                 Location/Qualifiers
REGION                  1..14
                        note = Anti-amyloid beta epitope identifying peptide
SITE                    1
                        note = MISC_FEATURE - X is pyroglutamic acid
SITE                    14
                        note = MISC_FEATURE - Biotinylation
source                  1..14
                        mol_type = protein
                        organism = synthetic construct
SEQUENCE: 35
XFRHDGGYEV HHQK                                                         14

SEQ ID NO: 36           moltype = AA  length = 14
FEATURE                 Location/Qualifiers
REGION                  1..14
                        note = Anti-amyloid beta epitope identifying peptide
SITE                    1
                        note = MISC_FEATURE - X is pyroglutamic acid
SITE                    14
                        note = MISC_FEATURE - Biotinylation
source                  1..14
                        mol_type = protein
                        organism = synthetic construct
SEQUENCE: 36
XFRHDSGGEV HHQK                                                         14

SEQ ID NO: 37           moltype = AA  length = 450
FEATURE                 Location/Qualifiers
REGION                  1..450
                        note = AC-264713 heavy chain sequence with C-terminal
                        lysine removed
source                  1..450
                        mol_type = protein
                        organism = synthetic construct
SEQUENCE: 37
EVQLQESGPG LVKPSQTLSL TCTFSGFSLS TSGMGVSWIR QPPGKGLEWL AHIYWDDDKR          60
YNPYMKRRLT ISKDTSKNQV SLKISSVTAA DTAVYYCARR ADDYDVGFAY WGQGTLVTVS         120
SASTKGPSVF PLAPSSKSTS GGTAALGCLV KDYFPEPVTV SWNSGALTSG VHTFPAVLQS         180
SGLYSLSSVV TVPSSSLGTQ TYICNVNHKP SNTKVDKKVE PKSCDKTHTC PPCPAPELLG         240
GPSVFLFPPK PKDTLMISRT PEVTCVVVDV SHEDPEVKFN WYVDGVEVHN AKTKPREEQY         300
NSTYRVVSVL TVLHQDWLNG KEYKCKVSNK ALPAPIEKTI SKAKGQPREP QVYTLPPSRE         360
EMTKNQVSLT CLVKGFYPSD IAVEWESNGQ PENNYKTTPP VLDSDGSFFL YSKLTVDKSR         420
WQQGNVFSCS VMHEALHNHY TQKSLSLSPG                                         450
```